(12) United States Patent
Mazzeo et al.

(10) Patent No.: US 9,612,140 B2
(45) Date of Patent: Apr. 4, 2017

(54) SUPPORT DEVICE FOR SENSORS AND/OR ACTUATORS THAT CAN BE PART OF A WIRELESS NETWORK OF SENSORS/ACTUATORS

(75) Inventors: Antonio Mazzeo, Pisa (IT); Alessio Misuri, Pisa (IT); Virginia Pensabene, Leghorn (IT); Sergio Scapellato, San Laazaro (IT); Pietro Valdastri, Leghorn (IT); Monica Vatteroni, Trento (IT)

(73) Assignee: WINMEDICAL S.R.L., Navacchio di Cascina Pi (IT)

( * ) Notice: Subject to any disclaimer, the term of this patent is extended or adjusted under 35 U.S.C. 154(b) by 576 days.

(21) Appl. No.: 12/921,275

(22) PCT Filed: Apr. 16, 2009

(86) PCT No.: PCT/IB2009/005264
§ 371 (c)(1),
(2), (4) Date: Oct. 4, 2010

(87) PCT Pub. No.: WO2009/127954
PCT Pub. Date: Oct. 22, 2009

(65) Prior Publication Data
US 2011/0021930 A1 Jan. 27, 2011

(30) Foreign Application Priority Data
Apr. 18, 2008 (IT) .................. PI2008A0032

(51) Int. Cl.
*A61B 5/02* (2006.01)
*G01D 11/30* (2006.01)
*A61B 5/00* (2006.01)

(52) U.S. Cl.
CPC ............ *G01D 11/30* (2013.01); *A61B 5/0002* (2013.01); *A61B 5/681* (2013.01); *A61B 5/6831* (2013.01);
(Continued)

(58) Field of Classification Search
USPC .................. 600/450–550; 455/100, 412; 340/539.11–24; 370/338
See application file for complete search history.

(56) References Cited

U.S. PATENT DOCUMENTS 4,141,351 A * 2/1979 James et al. .................. 324/692
6,356,952 B1 * 3/2002 Nagasawa ..................... 709/252
(Continued)

*Primary Examiner* — Michael Kahelin
*Assistant Examiner* — Mitchell E Alter
(74) *Attorney, Agent, or Firm* — Michael Best & Friedrich LLP

(57) ABSTRACT

A support device for sensors and/or actuators, of a node element or End Device (10) of a wireless network of sensors/actuators which support device comprises a base body or base module (1) with a plurality of faces (2), to which a sensor and/or actuator module or block (3) is mounted, and an electrical supply block/module (4). The main feature of the base body (1) is the possibility of adding to the node element (10) further sensors and/or actuators (3) as well as adapter elements, bridge interface elements (60) or expansion modules (50). The base body (1) can have a plurality of connection faces (2) with positive engagement means (54), which allow to assemble the above described modules. The positive engagement means (54) ensures an electromechanical connection between the many modules and, furthermore, assists an easy and intuitive accessibility for a user.

20 Claims, 18 Drawing Sheets

(52) U.S. Cl.
 CPC . *A61B 2560/045* (2013.01); *A61B 2560/0475* (2013.01); *A61B 2562/08* (2013.01)

(56) References Cited

U.S. PATENT DOCUMENTS

| | | | |
|---|---|---|---|
| 6,678,535 B1* | 1/2004 | Narayanaswami | 455/557 |
| 7,509,494 B2* | 3/2009 | Al-Ali | A61B 5/14551 |
| | | | 600/310 |
| 8,180,425 B2* | 5/2012 | Selvitelli et al. | 600/382 |
| 2002/0072682 A1* | 6/2002 | Hopman et al. | 600/509 |
| 2002/0084904 A1 | 7/2002 | De La Huerga | |
| 2004/0127802 A1* | 7/2004 | Istvan | A61B 5/0006 |
| | | | 600/509 |
| 2005/0265269 A1 | 12/2005 | Saito et al. | |
| 2006/0009697 A1* | 1/2006 | Banet et al. | 600/485 |
| 2006/0122466 A1 | 6/2006 | Nguyen et al. | |
| 2007/0027388 A1* | 2/2007 | Chou | A61B 5/0002 |
| | | | 600/393 |
| 2007/0282208 A1* | 12/2007 | Jacobs et al. | 600/485 |
| 2008/0081676 A1 | 4/2008 | Chakraborty et al. | |
| 2008/0177168 A1* | 7/2008 | Callahan et al. | 600/382 |
| 2008/0319327 A1* | 12/2008 | Banet et al. | 600/485 |

\* cited by examiner

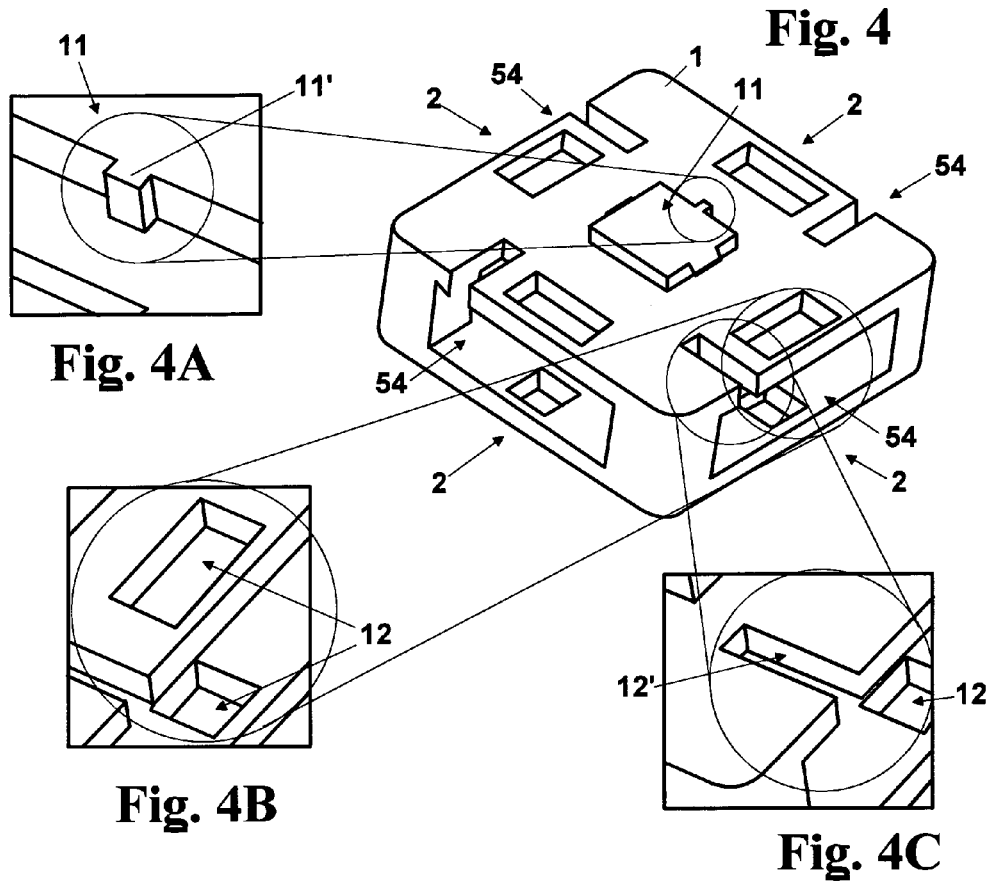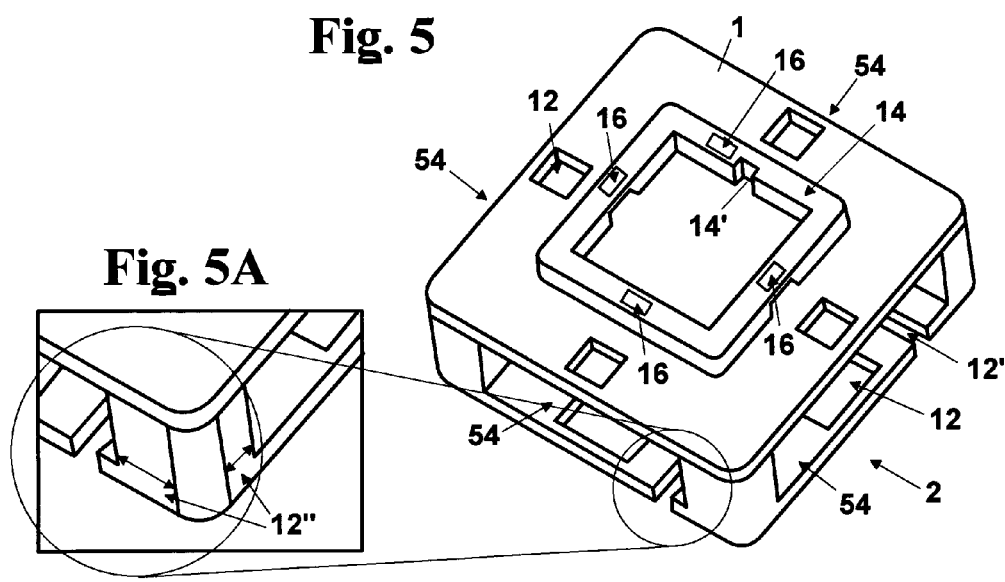

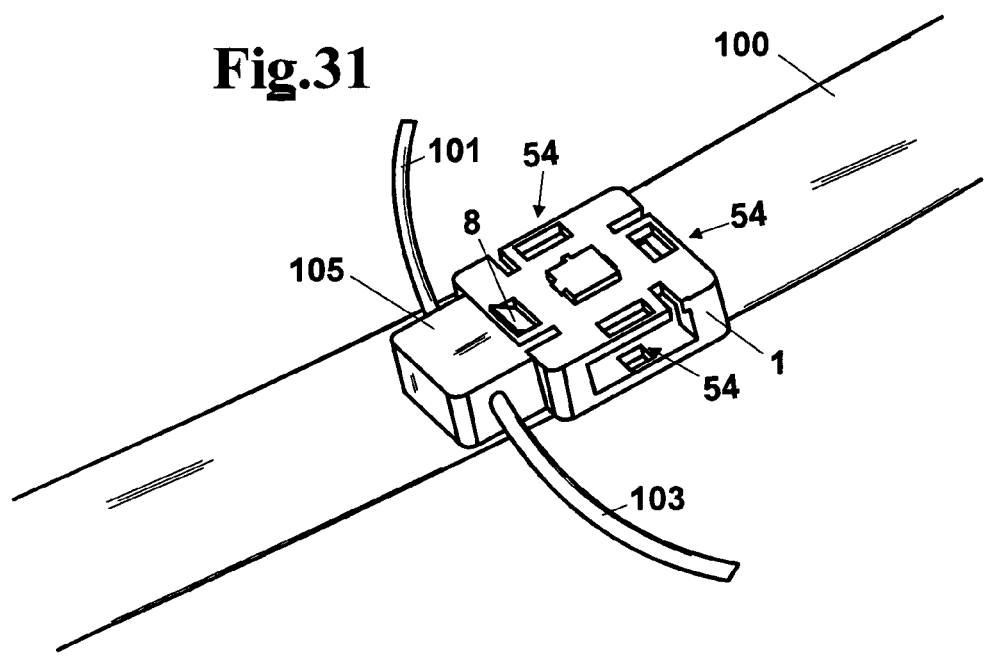
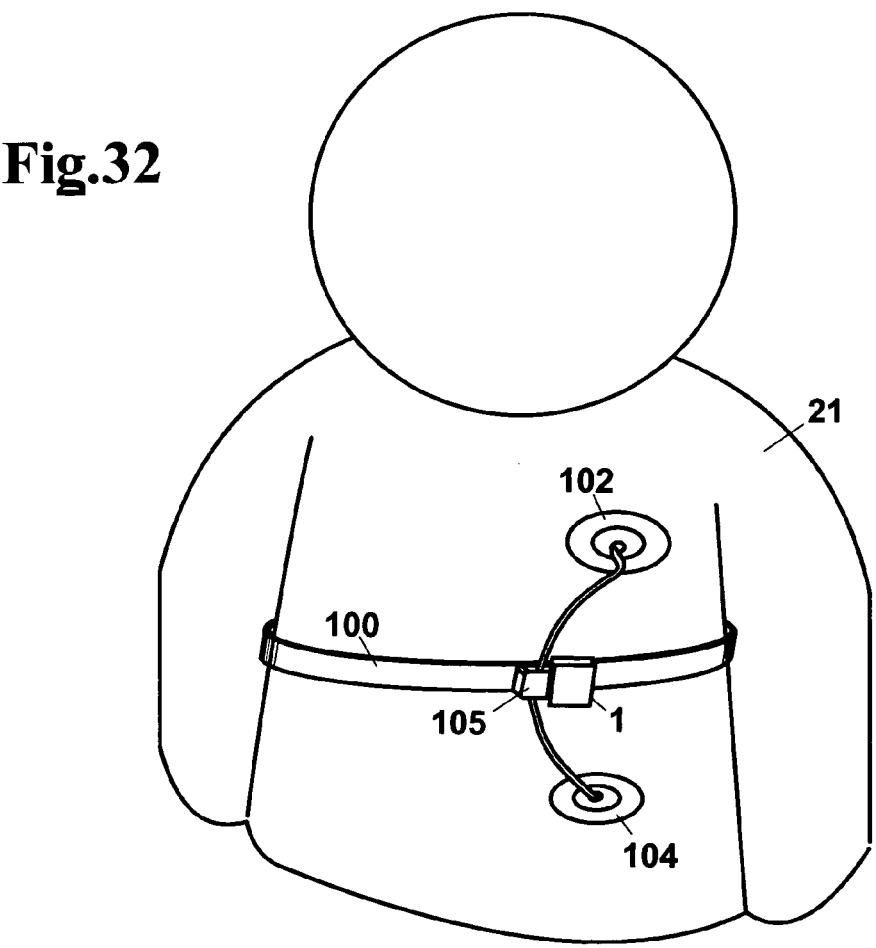

SUPPORT DEVICE FOR SENSORS AND/OR ACTUATORS THAT CAN BE PART OF A WIRELESS NETWORK OF SENSORS/ACTUATORS

FIELD OF THE INVENTION

The present invention relates to a device for monitoring and controlling wireless networks of sensors and/or actuators. In particular, this device is applicable in the biomedical field relating to a Wireless Body Area Network (WBAN) or Wireless Body Sensors Network (WBSN), for monitoring physiological parameters by means of sensors and/or actuators that are wearable by a patient.

DESCRIPTION OF THE TECHNICAL PROBLEM

Among traditional monitoring apparatus for patients, bulky and expensive systems are known that provide for each recorded parameter a respectively dedicated device. For this reason, the monitoring or sensing procedures can be carried out only by hospitals or health centers.

In such types of monitoring apparatus, the connection between the portable device, which is adapted to store and transmit data, and the sensors, which are adapted to detect the physiological parameters, is normally a wired connection. In particular, such sensors, which are put in contact with the skin of the patient, disturb the patient since the wiring limits the patient's movements.

The removal of wired connections is known, by using wireless communication and by low consumption power electronic technologies. In particular, networks are known of sensed knots, also known as computer network nodes or simply nodes, each having an own battery element and each arranged on the patient's body, which are capable to sense different physiological parameters, to store the parameters and/or to communicate the parameters in a wireless way to a more powerful device, which is capable of recording them and/or communicating them to a remote central operative unit.

Such devices are used, in particular, when monitoring physiological parameters by means of a system that is normally called "Wireless Sensor Network" (WSN).

A Wireless Sensor Network (WSN) is a network comprising small knots, which are capable of housing a sensor, of carrying out some computing steps on each knot and of communicating with each other through suitable network protocols. Such sensor networks are developed for applications that are typically dedicated to the nature of the data that are detected by the knots. In the biomedical field, for example, several data, like temperature, pressure, ECG signals, movement, position, blood pressure, etc., are measured. The WSN platforms are interesting owing to a plurality of features that are suitable for various types of applications. The main features of these networks are the following:
  stiffness of the knots that make them up: the knots have a reduced size that allows an easy positioning, according to the particular application;
  creating a network without the need of having a dedicated infrastructure;
  low energy necessary for operating the network, in such a way that batteries can be used, which have to last different years;
  heterogeneity of the knots and of the connectors;
  low computing capacity and communication of a single knot.

This type of networks, furthermore, are dynamic, since even if some knots break, or if the number of knots is changed, or in case of lack of battery, or if they are displaced, there are not relevant problems to the network.

The standard architecture of "Wireless Body Area Network" (WBAN) or "Wireless Body Sensor Network" (WBSN) provides different sensorized and miniaturized knots, each called "Body Sensor Unit" (BSU), also-called End Device, which are connected in a wireless way to a central unit that can be worn by the patient or located nearby, called Body Central Unit (BCU).

Specifically, the End Devices are the end knots of the network that are in contact with the patient's body or that are located in the surrounding environment, and that are equipped with a suitable sensor and/or actuator to carry out functions of monitoring and/or functions of active interaction with the patient.

The data obtained by the many BSUs are accessible online by a connection between the BCU and the Internet environment, which can be obtained by different technologies, such as WLAN, GPRS, UMTS, etc. This way, the patient who is monitored by the WBAN can be remotely surveyed by a doctor or by the hospital staff in a continuous way, in order to prevent possible complications. The data can be periodically stored in a dedicated server and a doctor can execute a complete check-up in any desired moment. In case of emergency, appropriate measures can be taken in short time, owing to an alarm, which can be activated both by the patient same, and owing to the monitoring system in response to any irregularities of the physiological parameters.

The limits/problems of an End Device, and in general of the biomedical WBAN products that are presently available on the market, can be the following:
  "closed" systems are presently available, where the user, such as doctor, nurse or the patient same, cannot modify the system structure;
  the End Devices have been designed and made according to a functionality that cannot be changed by the user unless with the aid of the producer/provider/supplier or of highly qualified operators;
  an End Device is defined and designed with a single function, which depends on the particular sensor/actuator that is mounted on it, without the possibility of adding or changing the particular measuring and/or operation functionality (for example the type of parameter to measure);
  The sensor/actuator, and/or the battery, is the only block that can be more or less easily replaced by the user, but only with very similar devices, i.e. with the same function.

These problems involve limits versus flexibility, since an End Device that is made for measuring a determined physiological parameter cannot be changed by the user in order to measure another parameter. This causes also a poor exploitation of the device, because once the system has completed its functions, or the parameter is not interesting any more, the whole device looses completely its utility and cannot be modified to carry out different functions.

SUMMARY OF THE INVENTION

It is therefore a feature of the present invention to provide a support device for sensors and/or actuators that can be part of a wireless network of sensors/actuators and that provides the possibility of integrating in a single knot a plurality of sensing and/or actuating components.

It is another feature of the present invention to provide such a support device for sensors and/or actuators that can be part of a context of Wireless Body Area Network (WBAN) or Wireless Body Sensors Network (WBSN) for monitoring physiological parameters by means of sensors and/or actuators wearable by the patient, which is adapted to support a plurality of sensors and/or actuators and at the same time can be easily fixed to the human body by adhesive means or other connection systems.

It is also a feature of the present invention to provide a support device for sensors and/or actuators that can be part of a wireless network of sensors/actuators that provides the possibility of integrating in a single point a plurality of sensors and/or actuators that can be used in domotic or industrial environments.

It is also a feature of the present invention to provide a support device for sensors and/or actuators which can be part of a wireless network of sensors/actuators that is modulable and reconfigurable regarding the components.

It is a further feature of the present invention to provide a support device for sensors and/or actuators that can be part of a wireless network of sensors/actuators in which an inexperienced user can choose and assemble sensing and/or actuator components of the device, according to the customized needs that derive from the patient's case or from results of previous detections or controls on the patient.

It is another feature of the present invention to provide a support device for sensors and/or actuators that can be part of a wireless network of sensors/actuators where the only sensing components of the device are developed in order to be minimally invasive for the patient and capable of interfacing in a user friendly way, with easy and plain connections.

It is also a feature of the present invention to provide a support device for sensors and/or actuators that can be part of a wireless network of sensors/actuators where the long term costs for of the device are low, such that the end user can purchase in different times the sensing components necessary and to replace each worn and/or unused block as well as to add new functionalities with the introduction other blocks, maintaining the same main framework.

These and other objects are achieved by a support device for sensors and/or actuators of a knot element of a network of sensing and/or actuating knots, comprising:
- a base body having a plurality of faces, to said base body at least one sensor and/or actuator and an electrical supply block being applicable;
- fixing means for fixing said base body to a support surface;
- a control unit in said base body comprising a microprocessor or micro-controller;
- a storage unit in said base body, said storage unit communicating with said control unit and adapted to store a plurality of configuration parameters, firmware and data;
- a wireless communication means that is adapted to make a Wireless Sensor Network bringing in communication said microprocessor with remote units, said remote units comprising other base bodies with respective sensors and/or actuators and at least one data control unit suitable to exchange signals with said base body, whose main feature is that
- at least two faces of said base body are connection faces of respective sensors and/or actuators, and that said base body comprises:
  - a positive engagement means, for making up a positive engagement between said sensors and/or actuators with said connection faces of said base body;
  - an interface means at said positive engagement means, for making up an interface between said sensors and/or actuators and said control unit;
  - an identification means for identifying a determined sensor and/or actuator connected to said base body by said positive engagement means and interface means.

In particular, said wireless communication means is arranged within said base body.

Preferably, said knot element of said network of sensing and/or actuating knots has reduced size, in the centimeter range. However, its scalable architecture allows to it a possible further miniaturization.

Advantageously, said base body has a flat shape, in particular, parallelepiped, with four substantially rectangular elongated connection faces, wherein at least one of said positive engagement means for making up a positive engagement between said sensors and/or actuators is at said rectangular connection faces.

Advantageously, an adapter element is provided, or "Front End" element, which can be fixed on said connection faces, said Front End element providing a positive engagement connection with at least one corresponding sensor and/or actuator, wherein said adapter element comprises one among the following elements or a combination thereof:
- a control unit comprising a microprocessor or microcontroller;
- a signal conditioning apparatus;
- a analog/digital and/or digital/analog converter;
- an interface with said base body;
- an identification device;
- an interface with said sensor and/or actuator.

Preferably, a bridge interface element is provided that connects respectively at least two base bodies, wherein said bridge interface element comprises one among the following elements or a combination thereof:
- a control unit comprising a microprocessor or microcontroller;
- a first interface with a first base body;
- an identification device;
- a second interface with a second base body.

This way, by the bridge interface element, it is possible to increase the number of the connection faces and therefore the number of sensors and/or actuators that can be connected. Furthermore, it is possible to increase the power and/or the functionality of the network knot element.

Preferably, said base body comprises at least one hardware input port, which is adapted to connection of auxiliary external devices such as, for example, a display for displaying the parameters that have been measured by said sensors, or memory expansion devices, etc. This way, with the display numerical values can be for example displayed, such as pressure, temperature, etc., but also images can be displayed: The memory expansion device, instead, can be necessary to boost the memory of the base body or the computing power, as well as for storing long term data, for example data of the patient on the 24/48 hours, for eventually uploading them at the end of the monitoring steps.

Advantageously, on said base body at least one battery element is provided that is engageable with one of said connection faces, said battery element adapted to provide electrical supply to said base body with the respective sensors and/or actuators, to any Front End elements, to any bridge interface elements and, to any auxiliary external devices.

In particular, said hardware input port is arranged at an upper face and/or a lower face of said base body.

Advantageously, a means is provided for engaging said battery element on said upper face and/or on said lower face of said base body.

In particular, said positive engagement means have a specific geometric shape in order to impede a wrong engagement by the user.

Advantageously, said identification means is selected from the group comprised of:
- analog identification means capable of measuring physical quantities;
- digital identification means (or based on digital data exchange).

Advantageously, said identification means provides start up means in said control unit to identify if a device has been plugged in said base body selected from the group comprised of: said sensor and/or actuator, said Front End element, said bridge interface element, an auxiliary external device, and to start a determined analog and/or digital dialog process.

In particular, said analog identification means measures a predetermined capacity of a condenser, or other physical feature of a passive circuit element, in order to identify univocally said sensor and/or actuator, or said adapter element or said bridge interface element connected to said base body, comparing said capacity or said other physical parameter with predetermined values.

Advantageously, said remote units are selected from the group comprised of: a mobile phone, a personal digital assistant, a computer, a home automation system or a server computer.

Preferably, said fixing means for fixing said base body to a support surface can be integrated on said base body, or in said sensors and/or actuators, or in said adapter element or, still in said bridge interface element.

In particular, said fixing means, in the medical field are selected from the group comprised of:
- a bracelet, which in particular can be fixed to an arm of a patient at the wrist;
- a belt, which in particular can be fixed to the torso of a patient;

wherein a portion of said bracelet and/or of said belt is connected to said base body at one or more connection faces by said positive engagement means. For example the bracelet or the belt may have in a direction orthogonal to their plane a connection portion to a connection face, or having two ends having two connection end portions to two opposite connection faces.

Advantageously, said bracelet has function of sensor and comprises a connection portion with a shape that positively engages with one of the connection faces of said base body. This way, the bracelet is in turn a monitoring sensor to which the base body is connected through one of its connection port surfaces; for this purpose, the bracelet can comprise one or more positive engagement portions, for example plug/socket click engagement portions for connection with the respective connection port surfaces of the base body.

In particular, said bracelet comprises a tonometric sensor, adapted to detect the "heart beat" of a patient, or more in general the blood pressure. In particular, said sensor comprises a detection surface that extends starting from the bracelet shaped connection portion.

Similarly, said belt has a function of sensor and comprises a connection portion with said base body. In particular, said belt comprises at least one couple of detection electrodes that extend starting from said connection portion for measuring the impedance of the patient's body.

Advantageously, said belt and said bracelet are adjustable in length and can be connected by a coupling portion with a housing that is made on said connection portion, which in addition to fasten the belt/bracelet to the patient, activates the operation of the integrated sensor.

Alternatively, said bracelet and/or said belt comprises two parts that are mutually connected by means of quickly releasable fastening means. This way, the bracelet and/or the belt can be adjusted and applied easily and quickly, without obstructing the movements of the patient.

BRIEF DESCRIPTION OF THE DRAWINGS

The invention will be made clearer with the following description of an exemplary embodiment thereof, exemplifying but not limitative, with reference to the attached drawings wherein:

FIGS. 4 and 5 and the respective enlarged partial views 4B, 4C, and 5A, show the positive engagement means adapted to connect the sensors and/or actuators, and the enlarged view of FIG. 4A shows a hardware type connection for connecting further expansion feeding modules, according to the invention;

FIGS. 16 and 16A show respectively an assembled view and an exploded view of a connection bridge between two respective base bodies, whereas FIG. 16B shows a connection bridge in a stacked form, according to the invention;

FIG. 18 shows a block diagram of the self-configuration steps of a base body when turning on;

FIG. 31 shows a particular view of FIG. 30 where it is shown the connection to the base body;

FIG. 32 shows a possible application of the belt of FIG. 30, applied to the torso of a patient for impedance detection.

DESCRIPTION OF A PREFERRED EXEMPLARY EMBODIMENT

Figure 1:
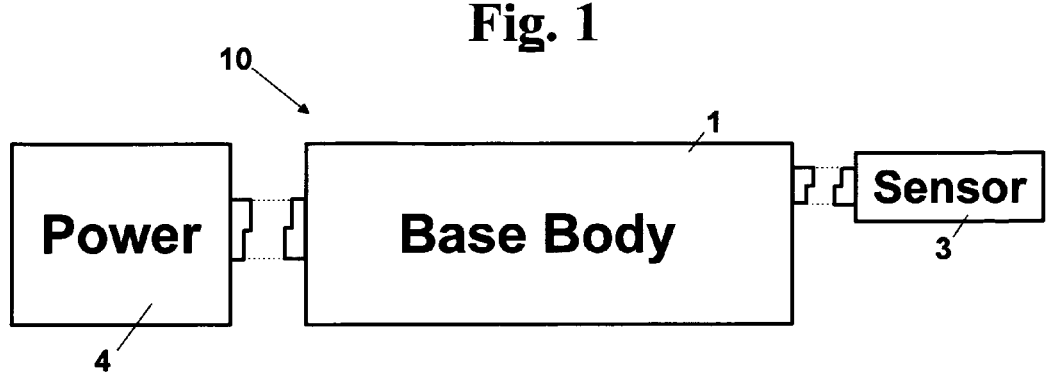
FIG. 1 shows a basic configuration of a knot element of a network of sensing and/or actuating knots or End Devices, comprising a support device for sensors, according to the invention.
Figure 1A:
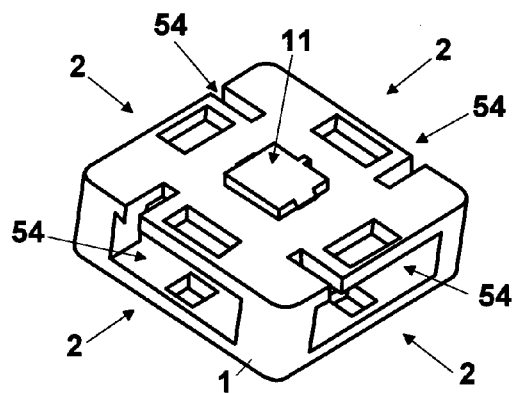
FIG. 1A shows the base body of the knot element of a network of sensing and/or actuating knots or End Devices of FIG. 1, of the connecting modular element, according to the invention.
Figure 3:
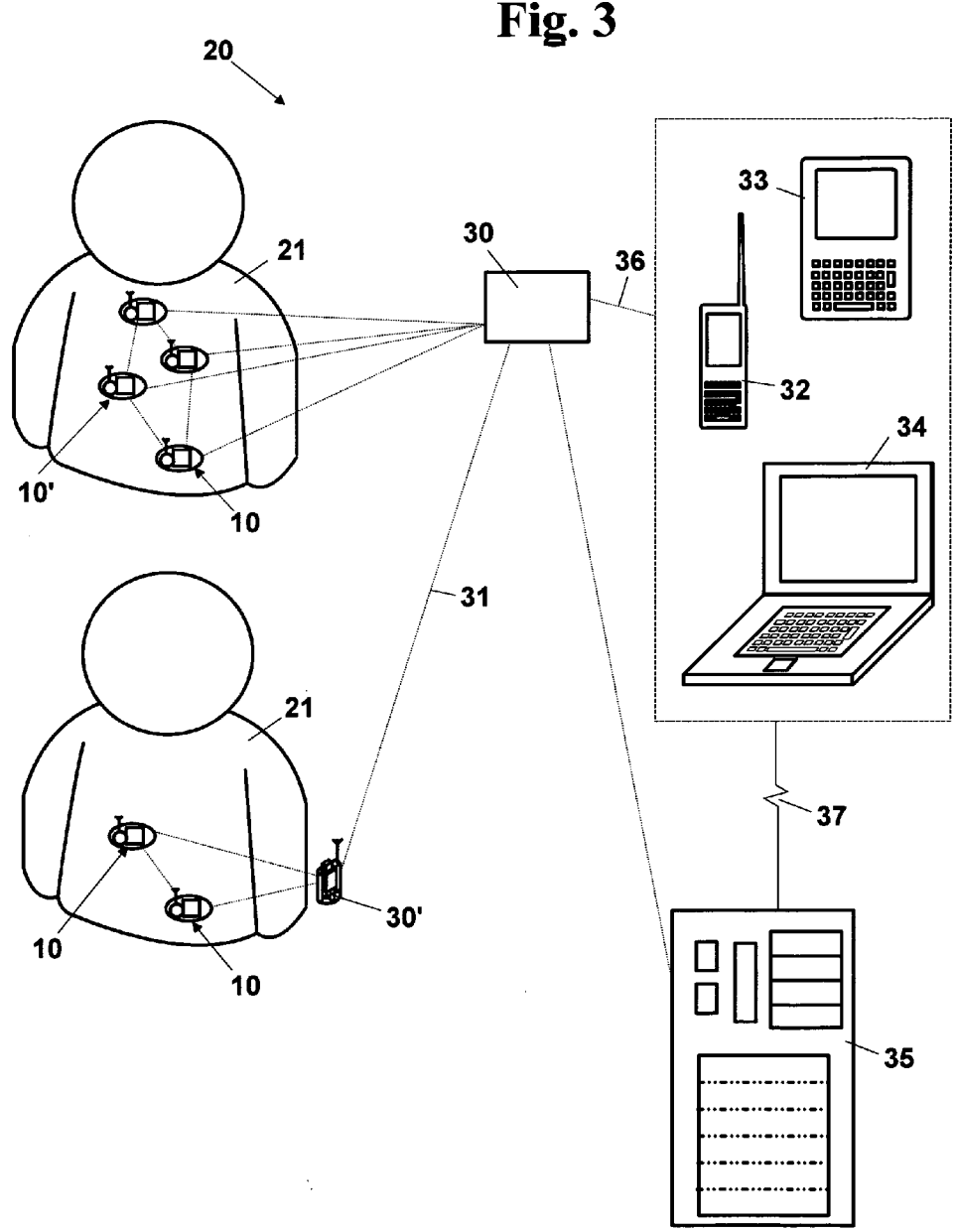
FIG. 3 shows a network of knot elements all having the basic configuration of FIG. 1, applied to a patient for monitoring, for example, physiological parameters.

With reference to FIGS. 1 and 1A a support device is shown for sensors and/or actuators, in a possible embodiment as a knot element or End Device 10 of a wireless network of sensors/actuators 20 (visible in FIG. 3). In particular, the structural architecture of End Device 10 has the peculiar feature of comprising a base body or base module 1, as shown in detail in FIG. 1A, having a plurality of faces 2, to which a sensor and/or actuator block/module 3 and an electrical supply block/module 4 are mounted. The main feature of base body 1 is the possibility of integrating knot element 10, by adding further sensors and/or actuators 3 as well as other electrical supply modules 4 or, yet, expansion modules as shown in the figures.

FIG. 1A shows the preferred parallelepiped flat shape of base body 1, with four substantially rectangular elongated connection faces 2 that provide a positive engagement surface between sensors and/or actuators 3 at each rectangular connection face 2.

Furthermore, auxiliary modules are provided, such as adapter elements 40, or Front End modules, which are arranged between sensor and/or actuator 3 and base body 1, an expansion module 50 (visible in FIG. 12) such as a display, a LED element, memory expansions, etc, as well as a bridge interface element or bridge module 60 (visible in FIG. 15) that capable of connecting together two base bodies 1.

Base body 1 comprises, furthermore, at any faces 2 that provide the connection surfaces, positive engagement means 54, adapted to receive respective sensors and/or actuators 3 or adapter elements 40 or bridge interface elements 60. In a preferred exemplary embodiment, positive engagement means 54 ensures an electromechanical connection between the many blocks and, furthermore, is made in order to allow an intuitive and easy accessibility for a user. A detailed description of the latter follows below.

In addition, each single sensor and/or actuator module or block 3 has an easy use and a compact appearance, so that the end user can assemble it without difficulty to obtain a final device with the desired features and functionality.

Furthermore, for example, a possible cover can be provided of the whole device 10 in order to seal it completely so that it can contact the body of a patient 21 (visible in FIG. 3) only at the sensor and/or actuator to modules 3.

Figure 2:
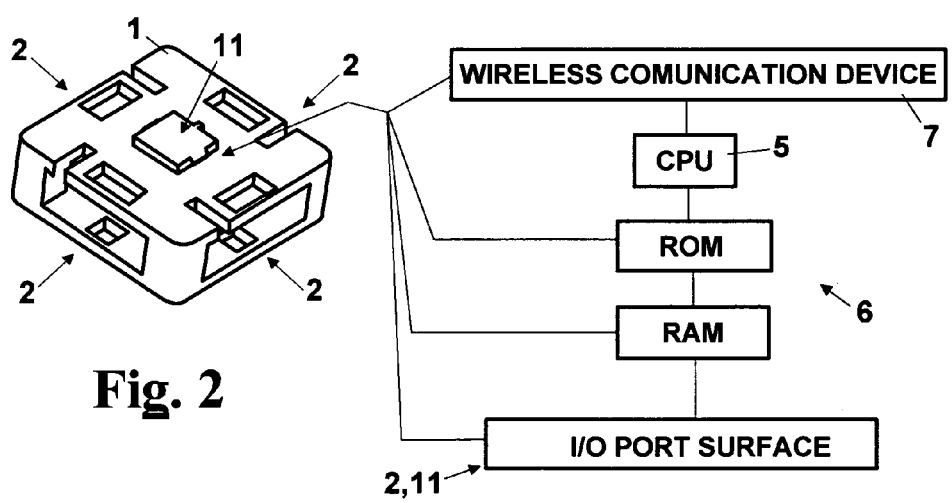
FIG. 2 shows a block diagram of the essential components present in the base body.

With reference to FIG. 2, the inner elements are shown that are necessary to the functionality and to the soundness of End Device 10 and that can be part of base body 1. In particular, such elements comprise a control unit 5 that contains a microprocessor (not shown), a storage unit 6 that communicates with the control unit 5 and stores a plurality of configuration parameters, a firmware, data, as well as a wireless communication means 7 that is adapted to make a Wireless Sensor Network (shown in FIG. 3) bringing the microprocessor in communication with remote units.

Figure 12:
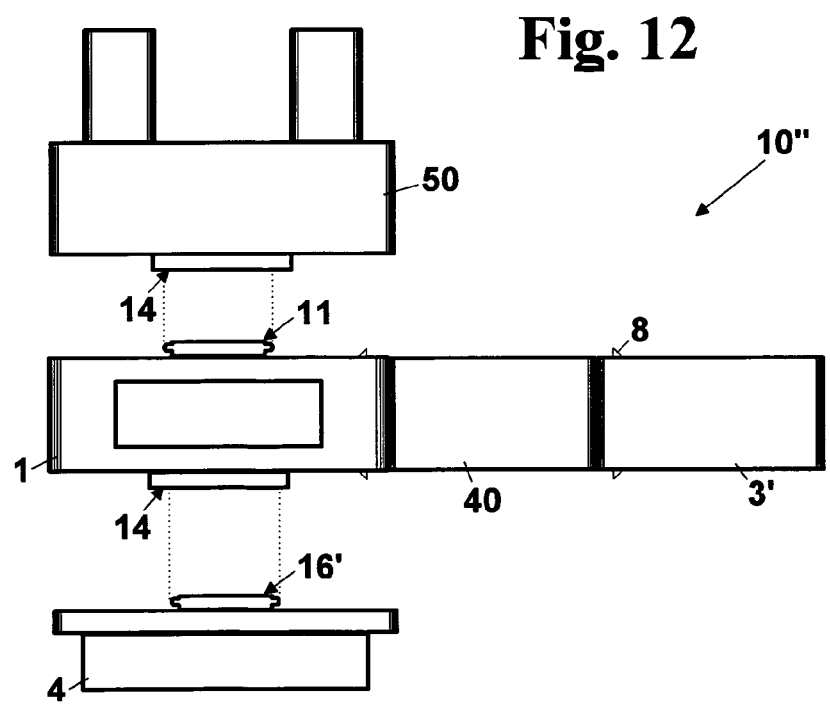
FIG. 12 shows an integrated support device, with a further element of expansion with respect to that shown in FIG. 9.

Furthermore, interface port surfaces 2,11 are provided that allow respectively a positive engagement with the connection means 54 of sensors and/or actuators 3 or of the adapter elements 40, but also of the bridge interface elements 60 and a hardware connection 11 with expansion elements 50 (shown in FIG. 12).

With reference to Wireless Sensor Network 20, the remote units, shown in FIG. 3, comprise other base bodies 1 with respective sensors and/or actuators 3 and relative electrical supply blocks 4 as well as at least one data control unit 30 that is suitable to exchange signals with base body 1.

In particular, base body 1 provides fixing means (not shown) for fixing it to a support surface, for example a patient 21 (visible in FIG. 3) whose physiological parameters are to or e monitored, or, in the domotic field, to a household surface for measuring a temperature, a pressure, etc.

FIG. 3 shows an example of a network of knot elements 20 that are adapted to measure, in the health care or domotic field, physiological parameters and other parameters. In particular, network 20 comprises a plurality of devices 10, in a basic configuration, which are arranged according to monitoring points that are determined of one or more patients 21.

Each End Device 10 comprises, then, an electrical supply block 4 and at least one sensor and/or actuator 3 mounted on the base body, according to the diagrammatical view of FIG.

1, by means of which a corresponding parameter is detected, such as temperature, pressure, heart beat, breath, etc. A particular case of pressure detection is described with reference to FIGS. 28, 28A and 29.

The possible ways with which base body 1 can be configured allow obtaining a knot element that is extremely flexible and that can be implemented to many applications, especially in the field of monitoring physiological parameters. In fact, the feature of replacing or integrating with respect to base body 1 sensors and/or actuators 3 with different functions, as well as the possibility of connecting a plurality of base bodies 1 to each other, allow developing a wide field of solutions.

Each base body 1 is, furthermore, connected in a wireless way to a data control unit or BCU 30 that can be also worn by patient 21, as a portable device 30'.

The data control unit 30 can be connected also to other control units, for example to portable device 30', in a wireless way, obtaining an data exchange network 31.

Concerning only BCU 30, it can comprise the same components of a base body 1 and can have, in general, a connection 36, of wired or wireless type, to a more powerful electronic device, such as a personal digital assistant 33, a mobile phone 32 or a personal computer 34 or directly to a remote server 35 by a connection 37. Typically, BCU 30 can have a size that is larger than base body 1 in order to house an electrical supply module 4 that is more powerful, unless more traditional cable electrical supply is provided.

According to the operation of each single base body 1 of network 20, base body 1 communicates with other base bodies 1 or with data control unit 30, which are to it physically connected, a possible priority index that is responsive to the pertinence of the data that each single knot element of the network has to transmit.

For example, in the medical field base body 1 can comprise an ECG sensor that has a priority higher than a base body that has a temperature sensor; this priority can evidently depend on the monitored pathology.

Vice-versa, the absence of communicating modules indicates the presence of a problem of base body 1 or simply the removal of sensor and/or actuator module 3. In this case, data control unit 30 is signaled to remove this base body 1 from a list of data to read, until a status change is possibly signaled by base body 1 same and a new initialization step is started.

With reference to FIGS. 4 and 5, a view of base body 1 is shown respectively according to a perspective view from the above and from below.

With reference to FIG. 4A a hardware connection 11 is shown, that is adapted to integrate base module 1 with expansion blocks 50 (shown in FIG. 12) or for connecting a base block 1 with another base block 1, as indicated in FIG. 16B. In particular, this hardware connection 11 is located on the upper face of base body 1 and has a corresponding port 14 on expansion module 50 (visible diagrammatically in FIG. 12) or on another base body 1 (visible in FIG. 5). This way, an engagement portion 11' and a respective cooperating portion 14' (shown in FIG. 5) identify univocally the connection. Port 14, in the lower part of base body 1, has, furthermore, electrical supply contacts 16 for connecting one or more electrical supply blocks 4.

FIGS. 4B, 4C and 5A depict an enlarged view of determined connection zones made on faces 2 of base body 1, showing positive engagement means 54 that is used for assisting the assembling step of the modules and to avoid mounting errors.

Figure 7:
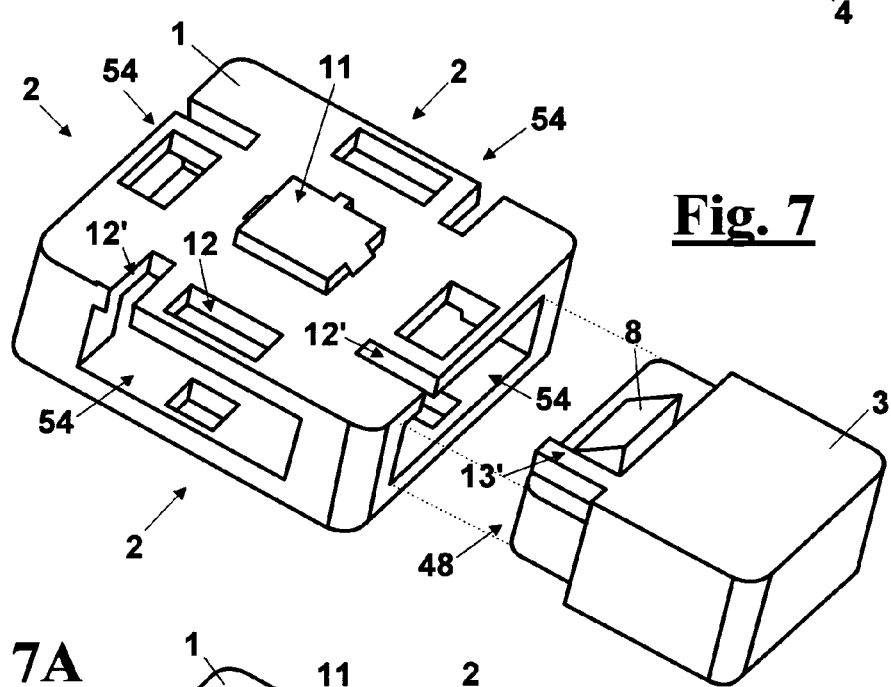
FIG. 7 shows an exploded perspective view of the device of FIG. 6 where, however, the supply battery is not visible.

In particular, positive engagement means 54 provides a recess 12 shown in FIG. 4B with which a respective fastening tooth 8 engages (visible in FIG. 7). This way, the user gently presses fastening tooth 8 to remove sensor and/or actuator 3 that had been previously inserted in base body 1. This exemplary embodiment is used also for connection between sensor and/or actuator 3' and Front End 40 (visible in FIG. 10) or for connection between base body 1 and Front End 40 or, still, for connecting bridge element 60 with two base bodies 1 (visible in FIG. 16).

Positive engagement means 54 provides, furthermore, a groove 12', as shown in the enlarged view 4C, that makes unique the connection and assists mounting sensor and/or actuator 3 by the user.

FIG. 5A shows a further element 12" that makes unique the connection of sensors and/or actuators 3 or adapter element 40 or, still, of bridge module 60, to base body 1. In particular, the distinction between the elements is that at a corner of base block 1 a different distance from an edge of interface port 2 responsive to the type of module that has to be connected is in turn made.

More precisely, base bodies 1 can be provided of a type that is adapted to engage with certain sensors and/or actuators, and then with ports that have predetermined width, and other base bodies can be provided of a type that is adapted to engage with other types of sensors and/or actuators, with ports that have different width. Thus, the sensors and/or actuators of the former base body type cannot fit the other base body type, assuring a unique connection.

Positive engagement means 54 may provide a number of connection pins respectively for the electrical supply of a module/block, for an automatic identification and for a bidirectional data communication of digital and/or analog type.

Also hardware input port 11 comprises a number of connection pins respectively for the electrical supply of the module, to enable a digital communication preferably of synchronous serial type and to allow an automatic identification, by base body 1, of the connected block as well as to carry out a bidirectional communication of data by means of dedicated communication protocols.

Figure 6:
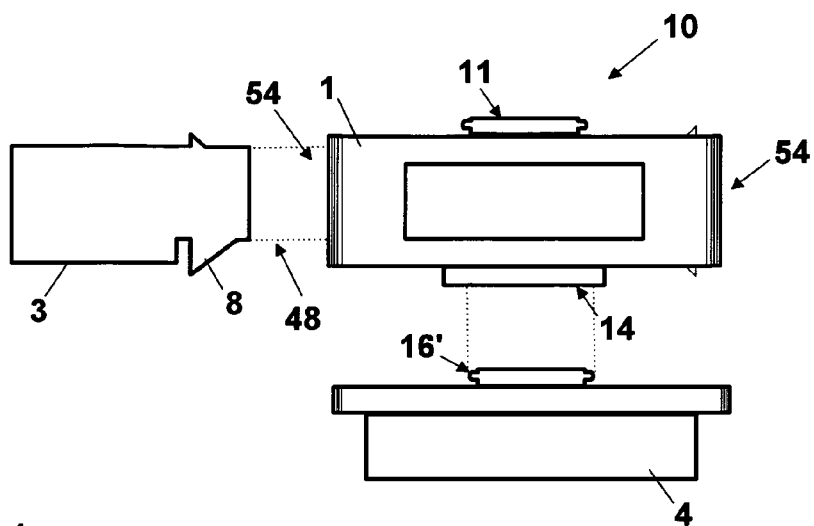
FIG. 6 shows an elevational side view of an End Device comprising a support device, a sensor and/or actuator, mounted laterally, and a battery element applied to its lower part.

FIG. 6 shows an elevational side view of the device as diagrammatically shown in FIG. 1, comprising a base body 1 to which respectively a battery element 4 and a sensor and/or actuator 3 are connected.

Figure 7A:
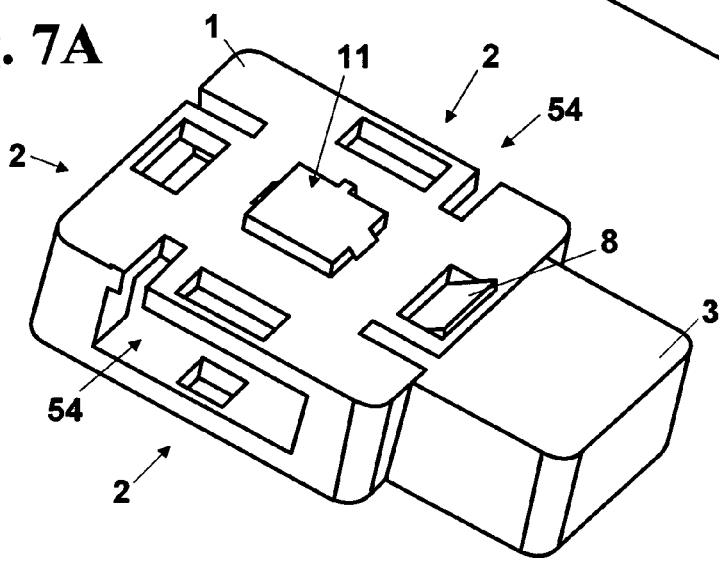
FIG. 7A shows a perspective view of the device of FIG. 7 in an assembled configuration.
Figure 10:
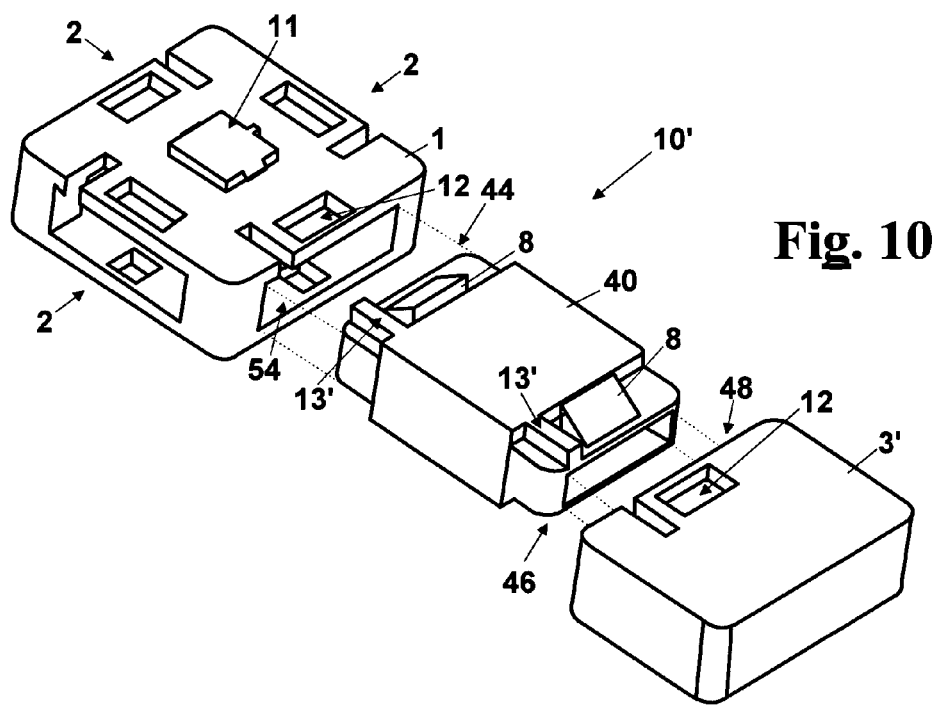
FIG. 10 shows an perspective exploded view of the device of FIGS. 8 and 9 where, differently, the supply battery is not shown.

FIGS. 7 and 7A depict corresponding perspective views of the device, respectively exploded and assembled, without showing the electrical supply module 4. In this configuration, sensor and/or actuator 3 has an engagement portion 48 that fits positive engagement means 54 that is present on faces 2 of base body 1. Furthermore, sensor and/or actuator 3 has a fastening tooth 8. This way, the connection is extremely easy and intuitive for the user, so that a connection cannot occur erroneously, since if sensor and/or actuator 3' an adapter element 40, as shown in FIG. 10, the respective positive engagement means 54 and engagement portion 48 would not fit with each other.

Figure 8:
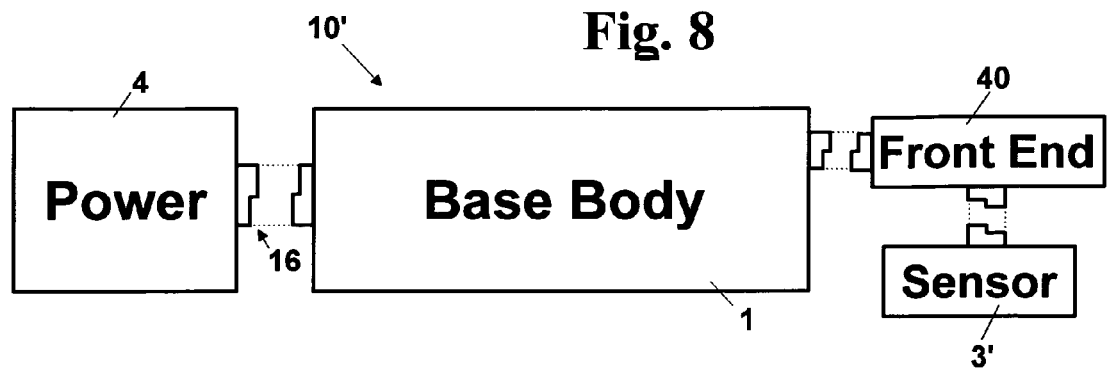
FIG. 8 shows a diagrammatical simplified view that comprises, with respect to that of FIG. 1, the adapter element or Front End element that is arranged between the sensor and the base body.

FIG. 8 shows a diagrammatical view of an End Device 10' that is equipped with an adapter element 40, or Front End module. In particular, as shown in the exploded view of FIGS. 9 and 10, End Device 10' provides respectively base body 1, Front End module 40, a sensor and/or is actuator module 3' and electrical supply block 4.

Figure 9:
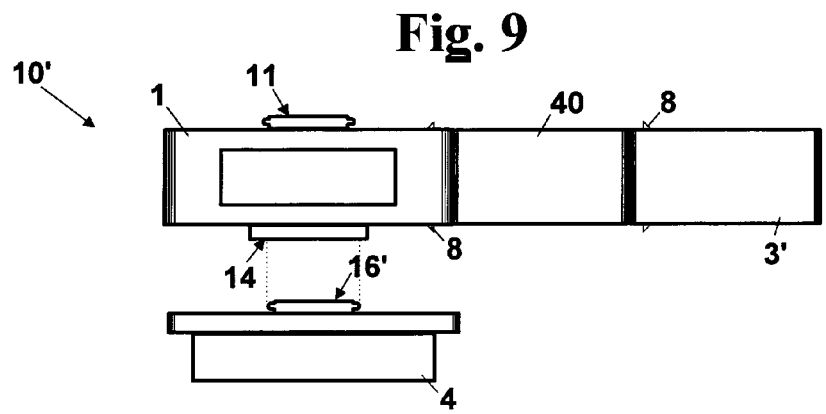
FIG. 9 shows an elevational side view of the device of FIG. 8 where it is shown the supply battery.

FIG. 9 shows an exemplary embodiment, in an elevational side view, of the device that is diagrammatically shown in FIG. 8. In particular, electrical supply block 4 is here visible as it is applied, by means of respective supply contact pins 16', under base body 1, whereas in the perspective view of FIG. 10, base body 1, adapter element 40 and sensor and/or actuator 3' are shown. In this exemplary embodiment sensor and/or actuator 3' has an socket engagement portion 48 that can engage the plug engagement portion 46 of Front End module 40.

This way, an inexperienced user cannot erroneously connect a sensor and/or actuator 3' that instead requires an interface element 40, directly to base body 1.

Figure 11:
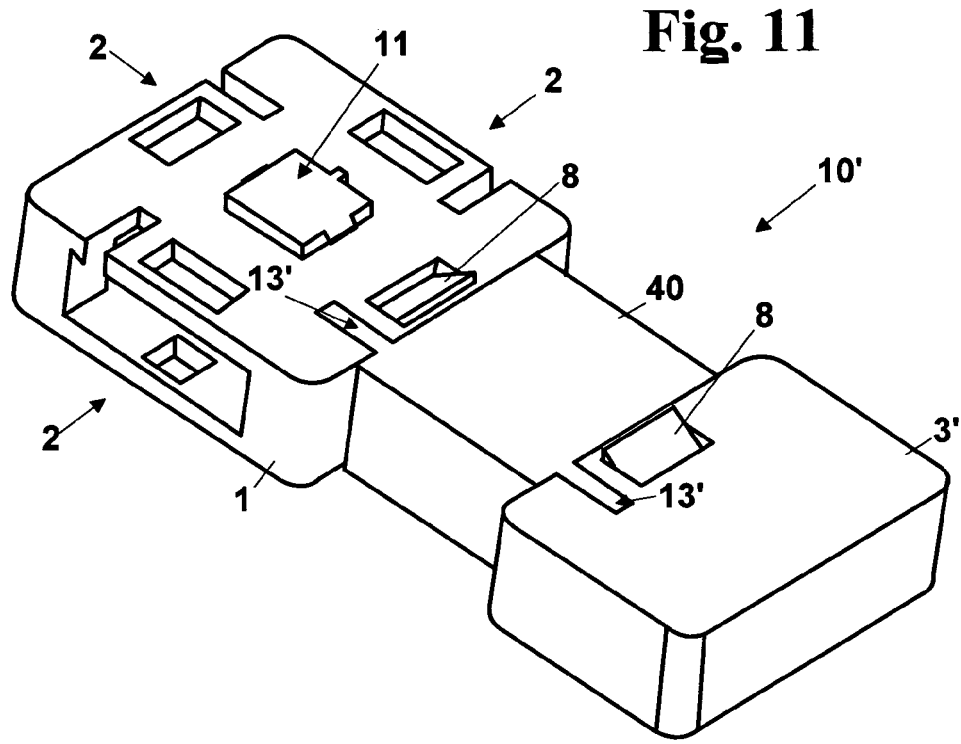
FIG. 11 shows an assembled view of the device of FIG. 10.

FIG. 11 shows the above described devices that are assembled to a single End Device 10' that is a further configuration of a knot element for monitoring network 20 of FIG. 3. In FIGS. 10 and 11 electrical supply block 4 is not shown.

FIG. 12 depicts an elevational side view of an end Device 10" comprising, in addition to that of FIG. 9, an expansion module 50 connected by hardware connector 11 and corresponding port 14 (visible in detail in FIG. 5). In particular, expansion module 50 can be selected from the group comprised of: display, timer, counter module, serial communication module, battery status monitoring block, memory expansion block, etc.

Figure 13:
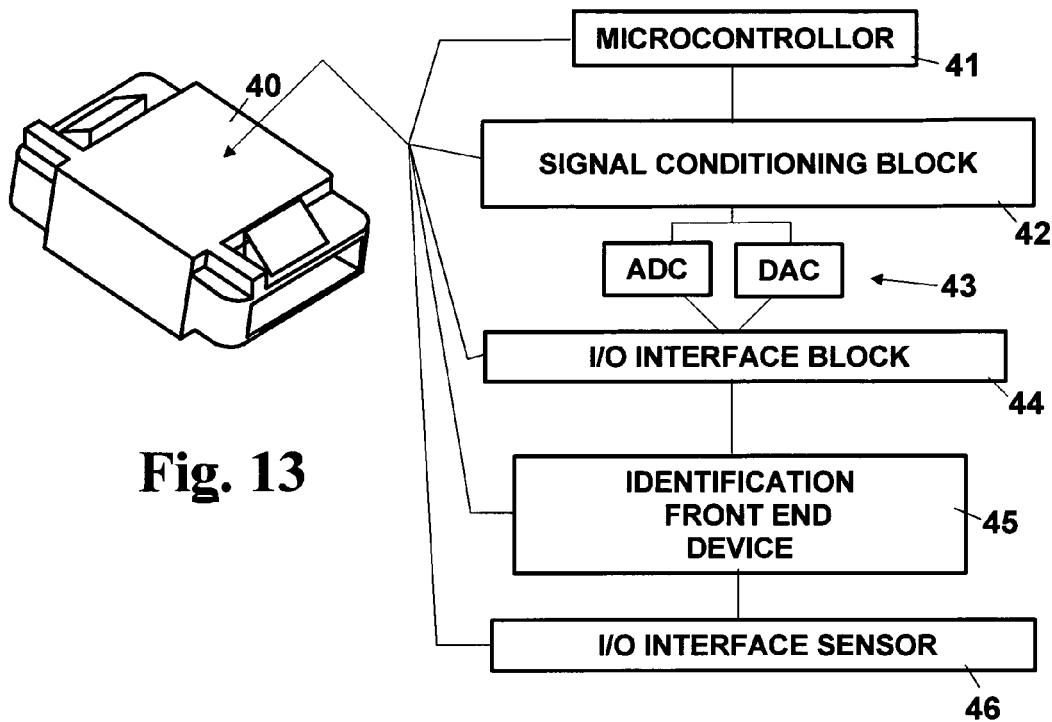
FIG. 13 shows a block diagram of the essential components of the adapter or Front End element that is located, in use, between the base body and the sensor and/or actuator.

FIG. 13 shows adapter means 40, or Front End module, which can be fixed to base body 1 at positive engagement means 54 between sensors and/or actuators 3' and base body 1.

In Front End module 40 at least the following hardware components have to be present: a microcontroller 41, a signal conditioning block 42, a analog/digital and/or digital/analog converter 43, an identification means 45 of the Front End element, input/output interface port 44 with base body 1 and at least one interface port 46 or input/output engagement portion with a sensor and/or actuator module 3'.

In particular, identification means 45 is selected from the group comprised of: analog means, capable of measuring physical quantities, or digital means, for example operating with dedicated communication protocols.

This way, microcontroller 41 is capable of driving signals coming from, or directed to, possible sensor and/or actuator modules 3' that are connected to adapter element 40. Microcontroller 41, furthermore, drives the modules identification part as well as the communication with base body 1.

Signal conditioning block 42 is adapted to condition the signals coming from possible sensor and/or actuator modules 3' that are connected to Front End 40. Such modules can comprise, for example, amplifier, multiplexer, switch, digital potentiometer circuit appliances, etc.

Concerning identification mechanism 45 of Front End module 40, it is desirable in the module so that base body 1 univocally identifies any adapter element 40 to it connected by interface port 44.

The same procedure is carried out for identification by Front End 40 of sensor and/or actuator 3' to which it can be connected.

Figure 14:
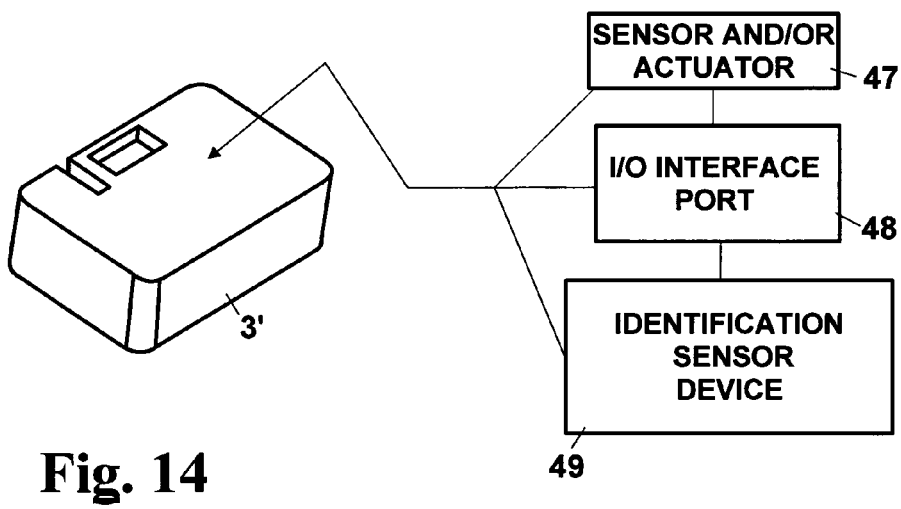
FIGS. 14 and 14A show a block diagram of the inner structural parts of the sensor and/or actuator.
Figure 14A:
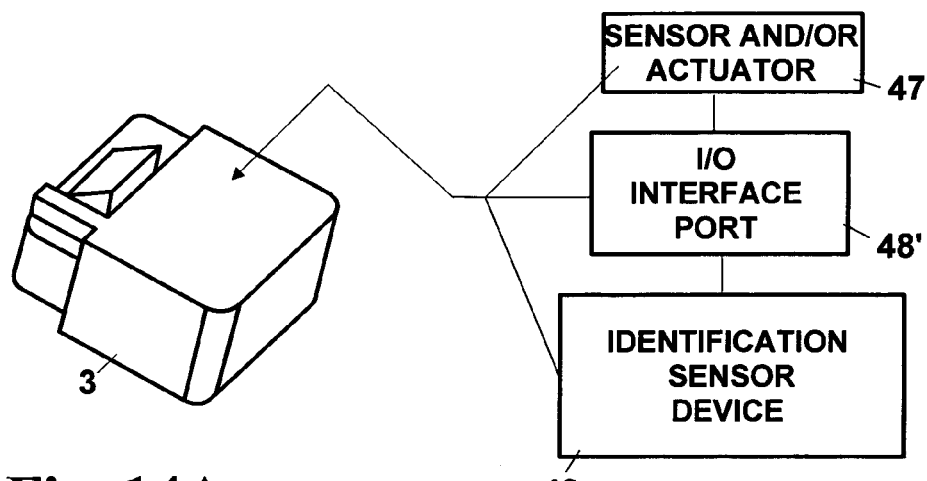

FIGS. 14 and 14A show respectively a sensor and/or actuator module 3' and a sensor and/or actuator module 3, which comprise, in particular, a sensor and/or actuator 47, an input/output interface port 48 or 48', which is an electromechanical part that connects respectively sensor and/or actuator module 3' with Front End module 40 and sensor and/or actuator module 3 directly with base body 1, and, like in the previous case, an identification mechanism 49 for identifying for sensor and/or actuator module 3', such that the module can identifying in a unique way the type of sensor and/or actuator 3' that has been connected at interface port 48. In particular, the connection port surfaces of interface 48 and 48' differ from one another depending on whether a Front End module 40 is necessary. The structural differences are shown, in use, in FIGS. 7 and 10.

Figure 15:
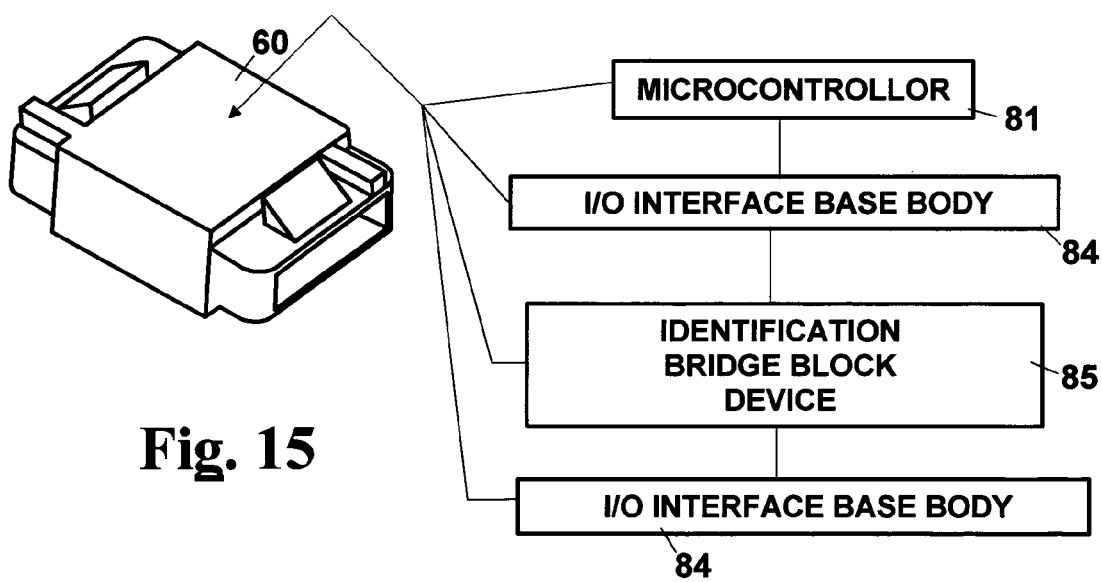
FIG. 15 shows a block diagram of the essential components of the bridge interface element that is located, in use, between two respective base bodies.
Figure 16:
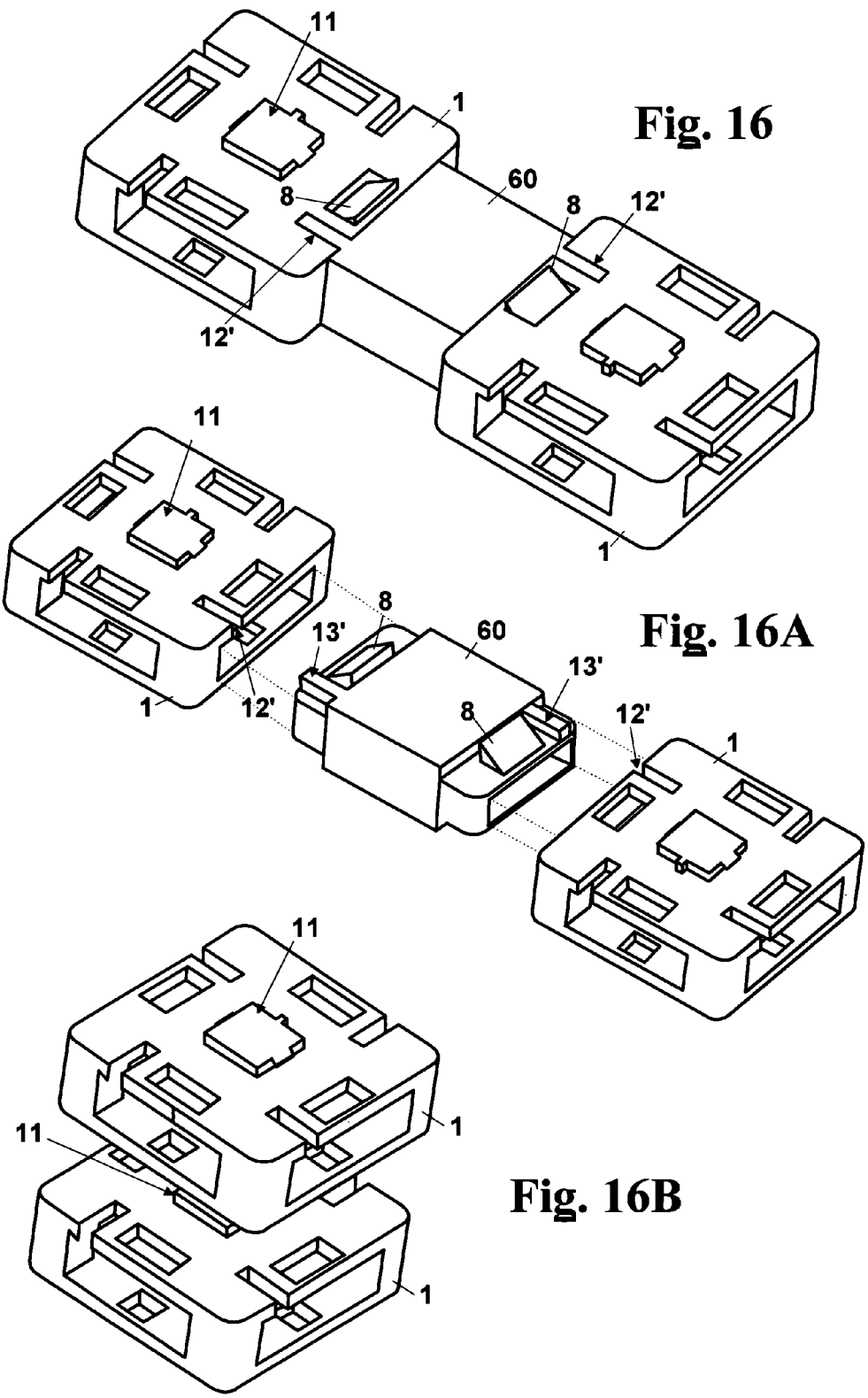

FIG. 15 shows the hardware components of bridge interface element or bridge module 60 that are the following: a microcontroller 81, an identification means 85 of the bridge module and two corresponding connection port surfaces for input/output interface 84 with two base bodies 1. A further possibility of connection, as it is visible in FIGS. 16 and 16A, provides a bridge interface element 60 (visible in FIG. 15) that connects respectively two base bodies 1 through a respective interface 84. This way, it is possible to increase the number of connection faces 2 and therefore the number of sensors and/or actuators 3 that are connectable. Furthermore, it is possible to increase the power and/or the functionality of each single knot element of the network 20.

The main differences between bridge module 60 and Front End module 40 are, on the one hand, in the different components as described in FIGS. 13 and 15, and, on the other hand, in their structural aspect, since the respective portions 13', which are on the same side of Front End 40, as shown in FIG. 10, are arranged at opposite sides in bridge module 60, in order to allow the connection of two base bodies 1. Alternatively, as shown in FIG. 16B, the connection between two base bodies 1 can be made by using hardware connection 11, in particular, combining port 11 to port 14 that is made on the lower part of base body 1 (visible in FIG. 5).

Figure 17:
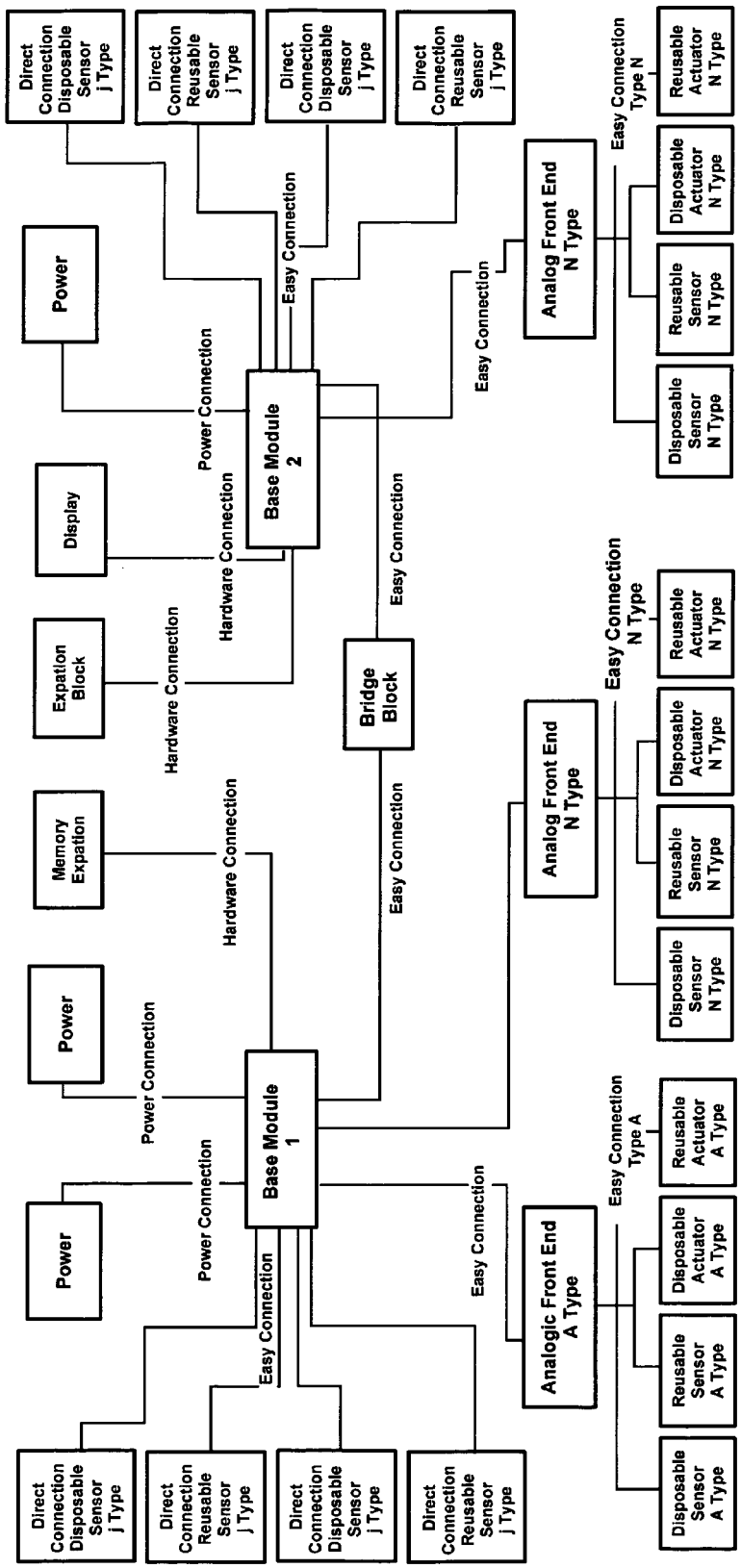
FIG. 17 shows a block diagram of a possible configuration of two base bodies that are integrated through the connection bridge of FIG. 16.

FIG. 17 shows a block diagram of the possible connection configurations between two base bodies 1 by bridge element 60.

In particular, each End Device 10 is normally composed by the following modules, shown in the block diagram:
base module 1;
sensor and/or actuator module 3 or 3', which may or may not have adapter element 40 for conditioning the signals;
Front End module or adapter element 40 for conditioning the signal;
electrical supply module 4 (in the figure it is called power);
bridge module 60, which is capable of connecting two base bodies 1;
possible expansion modules 50, which are capable of adding functions (expansion of memory, display, etc.) to base body 1.

The connection and the electromechanical connectors 54 between the above described blocks (shown in FIGS. 4 and 5) are made in order to ensure a "Plug & Play" intuitive procedure and an easy accessibility for a user.

In particular, the connection of the many modules to base body 1 is achieved by connecting firstly at least one electrical supply module 4 and is then the other modules without a specific order. An unique connection is ensured by the mechanical interface of key-lock type (shown in detail in FIGS. 4 and 5) that allow to distinguish among the many types of connected sensors and/or actuators. At the connection, the system may be turned on by a small key switch or turned on automatically as the first battery is plugged in.

Figure 18:
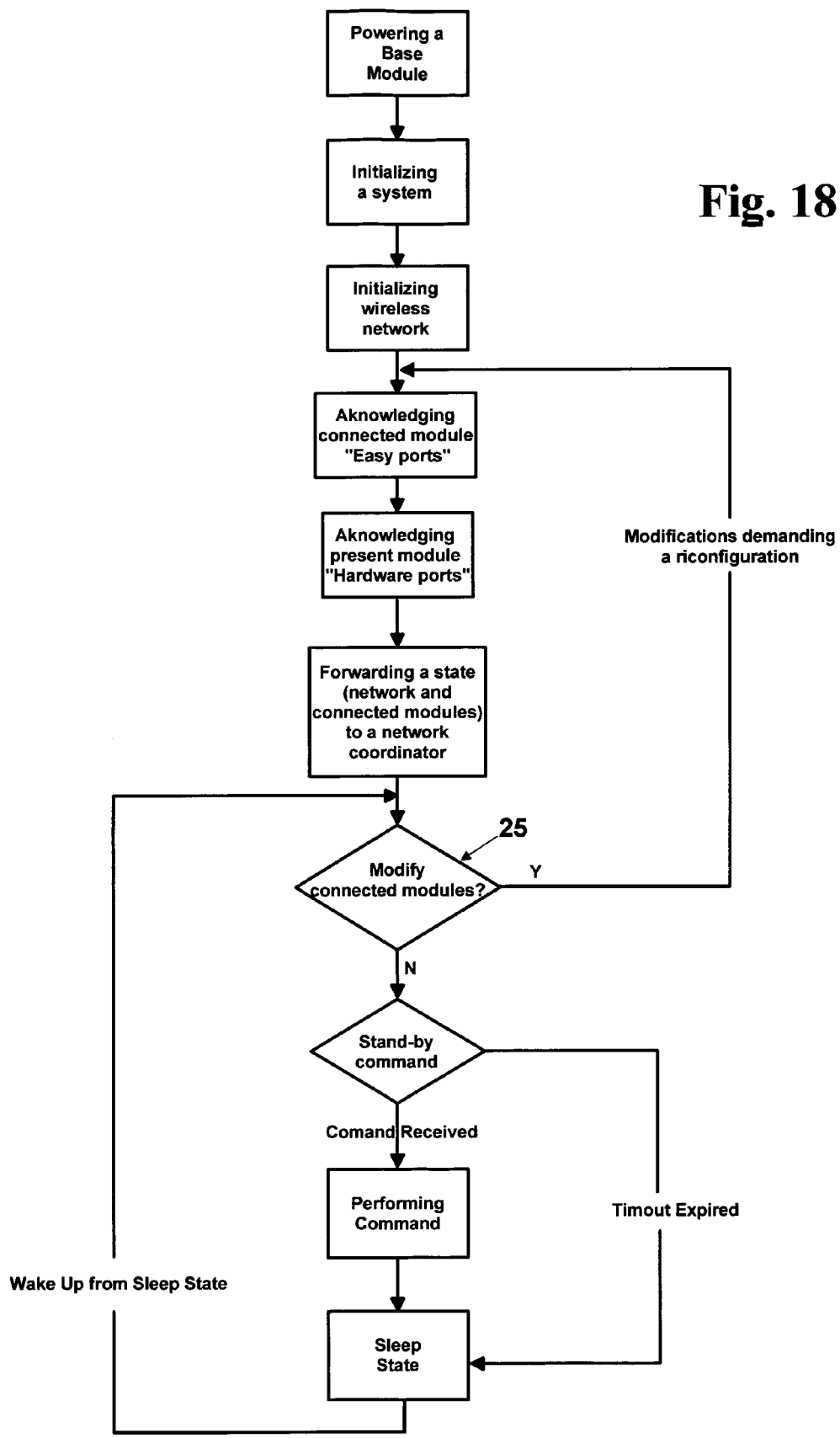

FIG. 18 shows a flow-sheet that describes the logic steps followed by base body 1 after turning on.

In particular, a microcontroller 5 that is present in base body 1 is programmed with a code (firmware) that ensures an extremely easy use by the end user and a full configurability of the whole system, both of single knot 10 and of whole network 20 (visible in FIG. 3), which consists of many single knots. Specifically a self-configuration system of a single base body 1 in the wireless network is provided that is triggered as the former is turned on, as well as a self-configuration system of the blocks connected to base body 1 is provided.

The flow sheet of the program, as diagrammatically shown in FIG. 18, provides the following steps:

1. turning on, i.e. connecting, first power module 4, or commuting a switch that is located on base body 1;
2. controlling the presence of a wireless network and possibly connecting to it;
3. controlling the presence of other connected modules to base body 1, following a procedure described hereafter;
4. transmitting the status (of the network and connected modules) to a network coordinator;
5. waiting for a command from the coordinator;
6. in case of receiving the command, executing the command;
7. starting a sleep mode, i.e. a low power consumption mode, and to returning to step 25 after a certain time.

The change of the network status and of the configuration status of the modules connected to the base body involves dedicated interruption subroutines and it triggers a re-start of the program from points 2 or 3 of the above described list.

When turning the system on, base body 1 begins a start up procedure during which it identifies the connected single modules and their functions.

Such start up procedure can be considered as standard for a microprocessor system since it simply defines the basic parameters of the controller that is provided on board. Then a step follows that is dedicated to starting up the radio parameters that are based on determined dedicated protocols.

A data updating step on the wireless network is provided at the end of the start up step; during this phase each single base body 1 of network 20, communicates to other base bodies 1 or to data control unit 30 which modules are to it connected and a possible index of priority according to the type of data that each single knot element of the network has to transmit.

Figure 19:
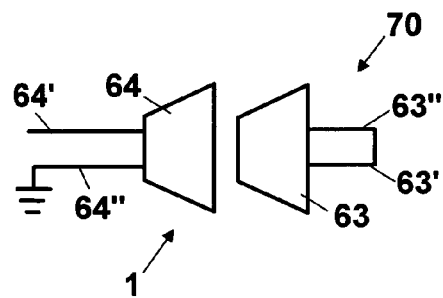
FIG. 19 shows a diagrammatical view of operation of how the base body can identify the connection of a module.

FIG. 19 shows the preferred mechanism according to which base body 1 learns that a module, of an a priori unknown type, is present on a face of interfaces 2 or 11 or 14. This event corresponds to step 26 of the diagram of FIG. 22. In particular, portion 64 represents two connection pins 64' and 64" from the edge of base body 1, whereas portion 63 represents two short-circuited pins 63'. and 63" that are present on sensor and/or actuator module 3, or on Front End module 40 or on bridge module 60, for connection to base body 1 by port 2, or to expansion module 50 for connection to base body 1 by port 11 or 14. More precisely port 64 is a subsystem of interface port 2, 11 and 14, whereas 63 is a subsystem of connection port surfaces of interface 44 or 48 or of interface port 44 of bridge module 60 or of interface port 14 of expansion module 50. A connection 70 is defined by portion 64 of the connector on the base side, since pin 64' is shirt-circuited to earth through connector 63 on the other side. Then, according to the distinction between modules that require an analog type connection identification 70 and modules that require a digital type connection identification 70', two identification different procedures are provided. In particular, the distinction is evaluated through the capacity of a condenser 65 or through the connection port surfaces 11 or 14 instead of port 2.

Figure 22:
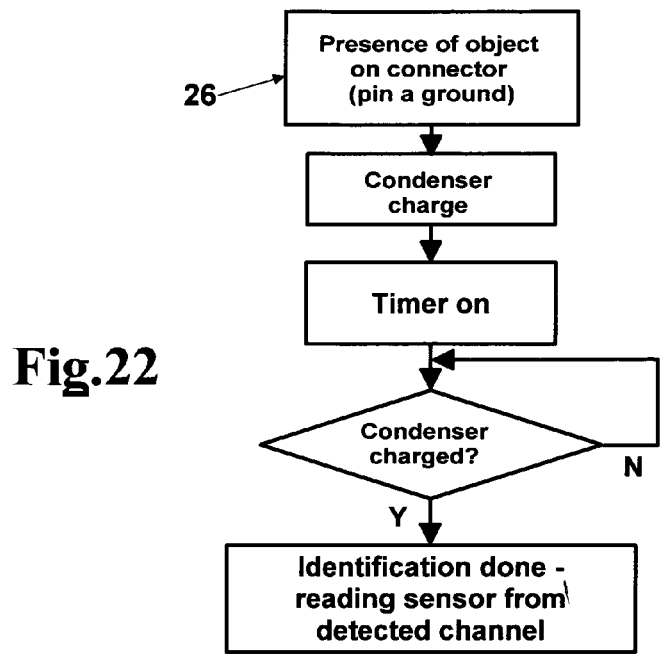
FIG. 22 shows a flow-sheet that describes the logical step sequence that is followed by the analog identification means.
Figure 24:
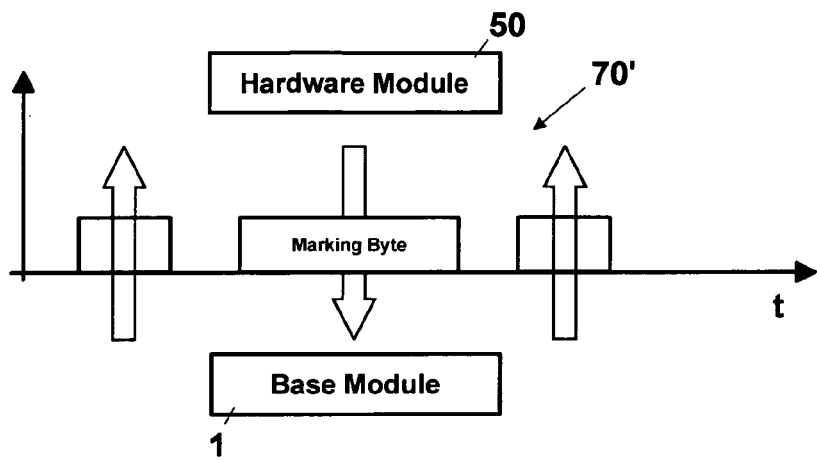
FIG. 24 shows a diagrammatical simplified view of the so-called handshake procedure of one of the blocks of the flow-sheet of FIG. 23.
Figure 25:
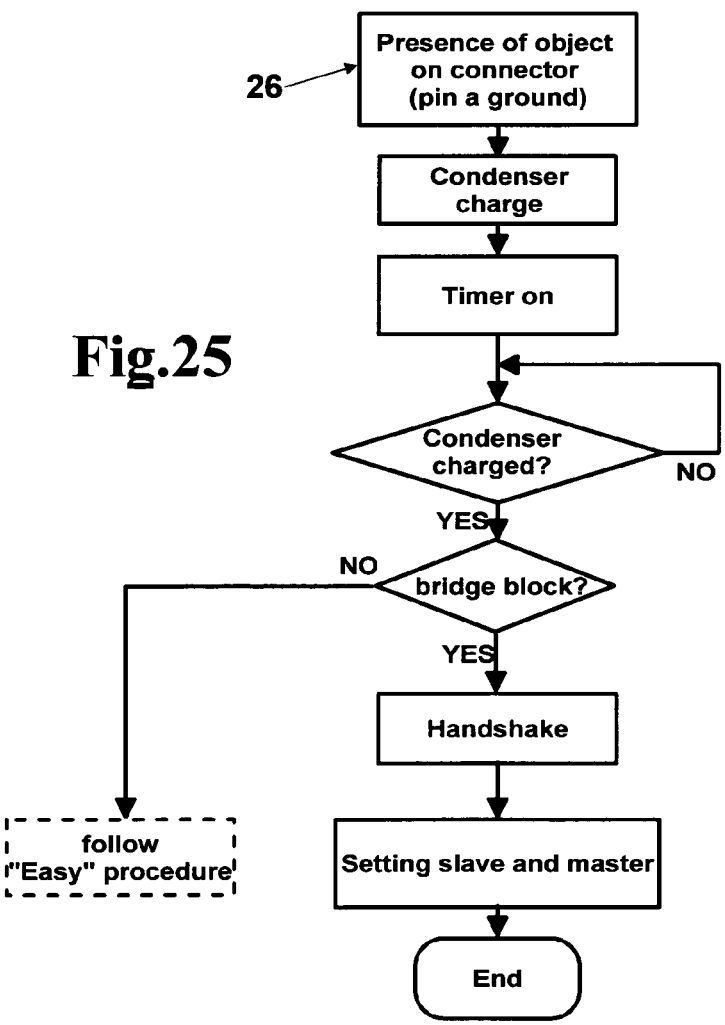
FIG. 25 shows a further configuration example that includes the connection bridge between two respective base bodies.

All the modules that are connected at the connection port surfaces 2 is execute a first analog identification step, as described in FIGS. 22 and 25, which is based on different values of the capacity of condenser 65. More complex modules, such as expansion modules 50, which require a digital identification mechanism, described in FIGS. 23 and 24, can be connected only at port 11 or 14 and then do not require condenser 65 for microprocessor 5 (visible in FIG. 2) of base body 1 to learn an analog or digital identification procedure to execute.

Figure 20:
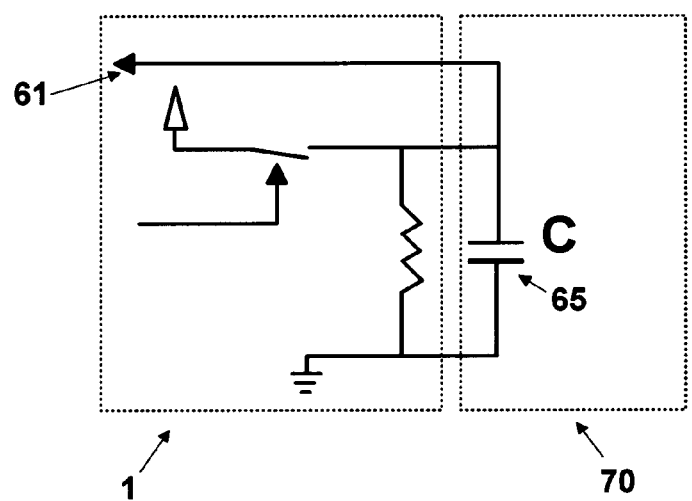
FIG. 20 shows an electrical scheme of an exemplary embodiment of the analog type identification means, which is arranged between the base body and a module that is selected from the group comprised of: sensor and/or actuator, interface element or bridge connecting element.

FIG. 20 shows an analog identification step 70 of the modules, as it is carried out through a process of automatic charge, when the connection succeeds, and discharge, activated by a pin of base module 1, of a condenser 65. The process of discharge is detected and measured as the time that it is necessary for the voltage on condenser 65 to fall below a certain threshold, through an input pin 61 of base module 1. The capacity of distinguishing between two different modules, which belong to a same kind of connection 70, is achieved by the different capacity value of condenser 65 as it is mounted on different modules.

Figure 21:
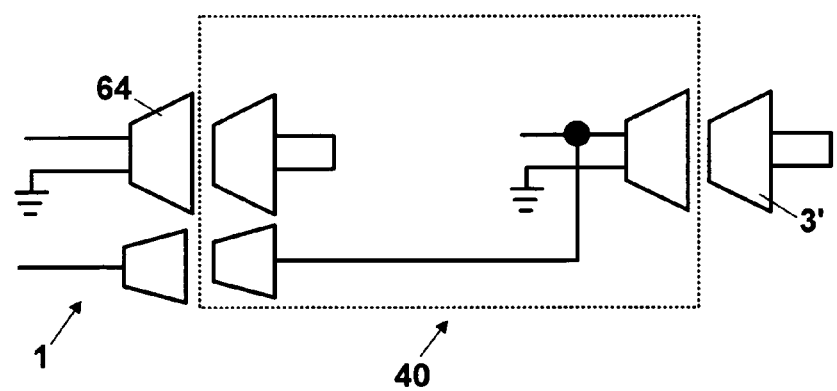
FIG. 21 shows an exemplary embodiment of FIG. 19 extended to the case where the identification of an occurred connection of a module includes the interface adapter element or Front End element that is arranged between the base body and the sensor and/or actuator.

FIG. 21 shows how both microcontroller 5, which is present in base block 1, and microcontroller 41, which is present in Front End module 40, can realize at the same time, using a minimum number of electrical connections, of an occurrence of a "connection status" between a sensor and/or actuator 3' and Front End module 40 through interfaces 46 and 48. Once it has been identified, microcontroller 41 drives a procedure similar to that shown in FIG. 20, where condenser 65, however, is in this case on board of sensor module 3' that is connected to Front End module 40 and the charge and discharge of condenser 65 is operated by microcontroller 41, which is present in Front End module 40. Once effected the identification, microcontroller 41 digitally communicates to microcontroller 5 the nature of the connected sensor and/or actuator 3'. In this case, base module 1 signals to Front End module 40 to start a configuration step, which is operated by a microcontroller 41 that is inserted on board of Front End module 40, by the charge of a condenser (not shown) that is operated via pin 64 of base body 1. Once identified the configuration starting signal (condenser is charged) microcontroller 41 proceeds to start a similar charge and discharge procedure with respect to the connected sensor and/or actuator.

The absence of a sensor and/or actuator 3' connected to Front End module 40 represents an error condition that is signaled to base body 1 through a suitable digital line, which is configured as shown in FIG. 21; the change of status of this line signals to base body 1 that an error condition has been resolved.

FIG. 22 shows a flow sheet of a sequence of logical steps that are adopted for an analog identification procedure, as above described, of the many sensors and/or actuators 3 as well as of Front End module 40.

Figure 23:
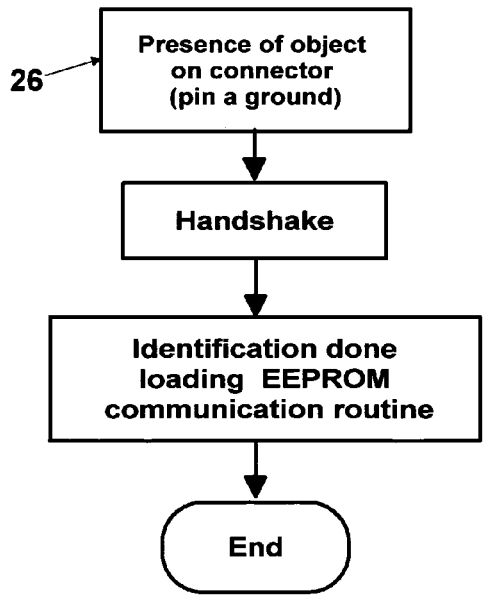
FIG. 23 shows a respective flow-sheet of the logical step sequence that is followed by the digital identification means.

FIG. 23 shows a flow sheet of a sequence of logical steps that are adopted for a digital identification procedure as it is operated by base body 1 of expansion modules 60 or by other base bodies 1 that are connected at the connection port surfaces 11 and/or 14 of said base body. The solution that is depicted in the above described flow sheet provides a so-called handshake step that is carried out on a single wire, which is dedicated to the digital identification between two modules. In particular, base body 1 activates a pin, which is configured as output, connected to a pin, configured as input of the "hardware" module or expansion module 50, which, before responding with a bit succession that identifies the type of modules that has been connected, converts the pin on which it has received the signal into a output pin. Similarly, base body 1 converts its output pin into an input pin for receiving the message, after a determined time. A following conversion of the pin allows to base body 1 to acknowledge a correct receipt of the message with a further impulse. The whole communication process is synchronized through a clock signal that is generated by base body 1 and that is sent by a pin that id dedicated to the module 50 connected on an interface port 11 or 14.

FIG. 24 diagrammatically depicts the above described data flow of the so-called handshake step, as indicated in FIG. 23 for identifying expansion modules 50 or other base bodies 1 that engage with the connection port surfaces 11 or 14 of base body 1. In this case an analog identification, as in the previous case, is not sufficient, since they are devices of many different kinds, such as a display, an external memory, interface elements of many kinds, etc., which could require complex communication protocols for communicating with base body 1.

With reference to FIG. 25, a flow-sheet is shown that represents the identification steps of bridge block/module 60.

Figure 26:
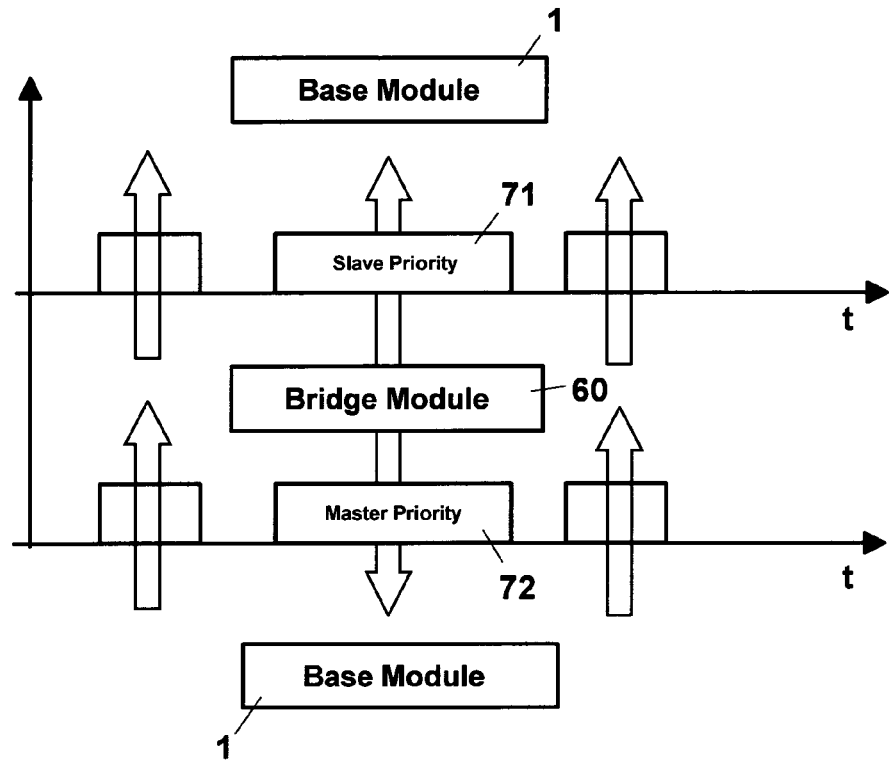
FIG. 26 shows a diagrammatical simplified view of the handshake procedure of one of the blocks of the diagram of FIG. 25, effected in case of a connection bridge.

FIG. 26 shows in detail the digital data flow during a so-called handshake step, as it is indicated in the flow-sheet of FIG. 25. In this case, bridge module 60 connects two base bodies 1 through the respective connection port surfaces of interface 2, also shown in FIG. 16. As indicated in FIG. 25, once bridge block 60 is identified by two base bodies 1 to which it is connected, a handshake procedure starts in which to two base bodies 1 are given, by bridge block 60, the functions as master 72, i.e. acquisition and transmission via radio of all the data, as well as the functions as slave 71 i.e. acquisition and transmission of data by bridge 60 to master 72.

Figure 27:
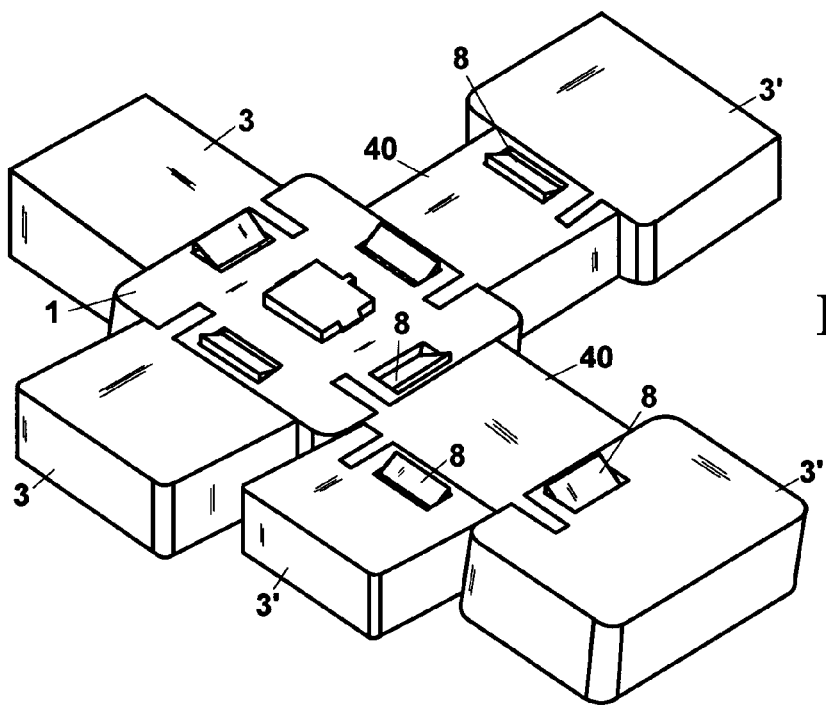
FIG. 27 shows a support device that is equipped, on the connection faces, with respective sensors and/or actuators with or without the interface element.

FIG. 27 shows a base body 1 to which on all connection faces 2 respective sensors and/or actuators 3' and 3 are connected respectively with and without the aid of Front End 40. This solution has several advantages, such as the possibility to replace sensors and/or actuators 3, with other modules having different functions, connected to base body 1, as well as the possibility to provide many other configurations for any monitoring and/or operating function in the medical and/or domotic field.

In particular, in the medical field a fixing means is selected such as a bracelet 80 (FIGS. 28 and 28A), which can be fixed to the wrist 90 of a patient (FIG. 29), or a belt 100 (FIGS. 30 and 31), which can be fixed to the torso of a patient 21 (FIG. 32).

Both types of fixing means are used for monitoring/measuring physiological parameters in a patient.

Figure 28:
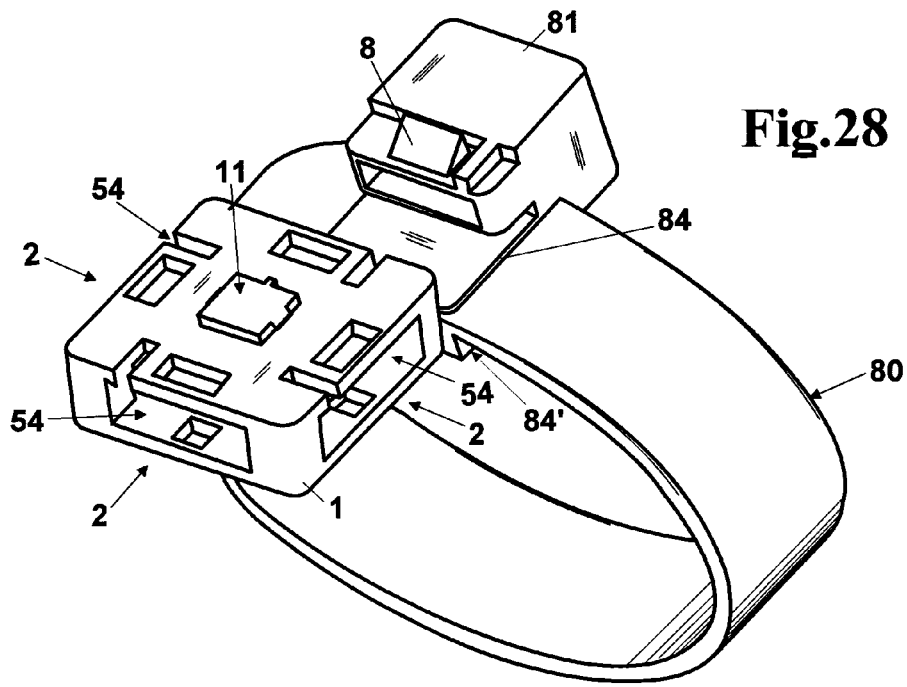
FIGS. 28 and 28A show a sensorized bracelet for measuring blood pressure which can be fixed to the wrist of a patient, in particular, the two figures show the connection with the base body.
Figure 28A:
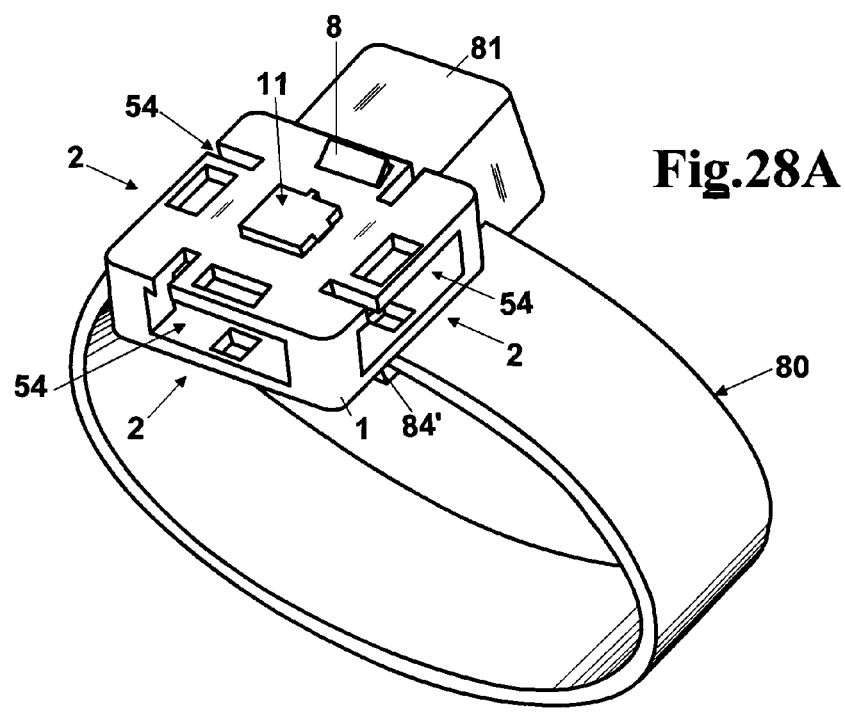
Figure 29:
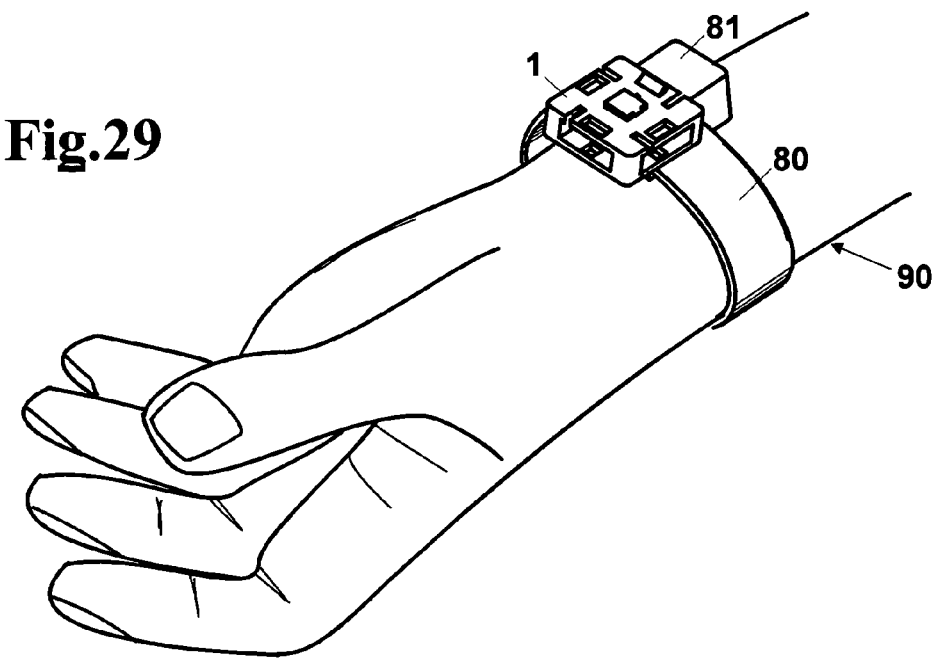
FIG. 29 shows a possible application of the bracelet of FIG. 28 for measuring the "heart beat" of a patient.

In the example of FIGS. 28 and 28A bracelet 80 has function of sensor adapted to detect the "heart beat" of the patient or, more in general, the blood pressure. Structurally, then, the bracelet comprises an inner monitoring sensor 84 and a connection portion 81 with which base body 1 is connected through one of connection ports 54 (FIG. 28A). More precisely, the positive engagement connection portion 81 for connection with base body 1 has a fastening tooth 8 that engages with a connection port 54 of base body 1.

More in detail, sensor 84 comprises a detection plane 84' (not shown in detail) that protrudes from connection portion 81 and, in use, contacts the patient's radial artery. This way, the application to base body of the sensor 1, and of other possible sensors and/or actuators, is easy and effective and allows to modify the device as desired. Further advantage, in addition to modularity, is the size more compact than the known devices such that the patient can easily carry the bracelet even for a long time.

Figure 30:
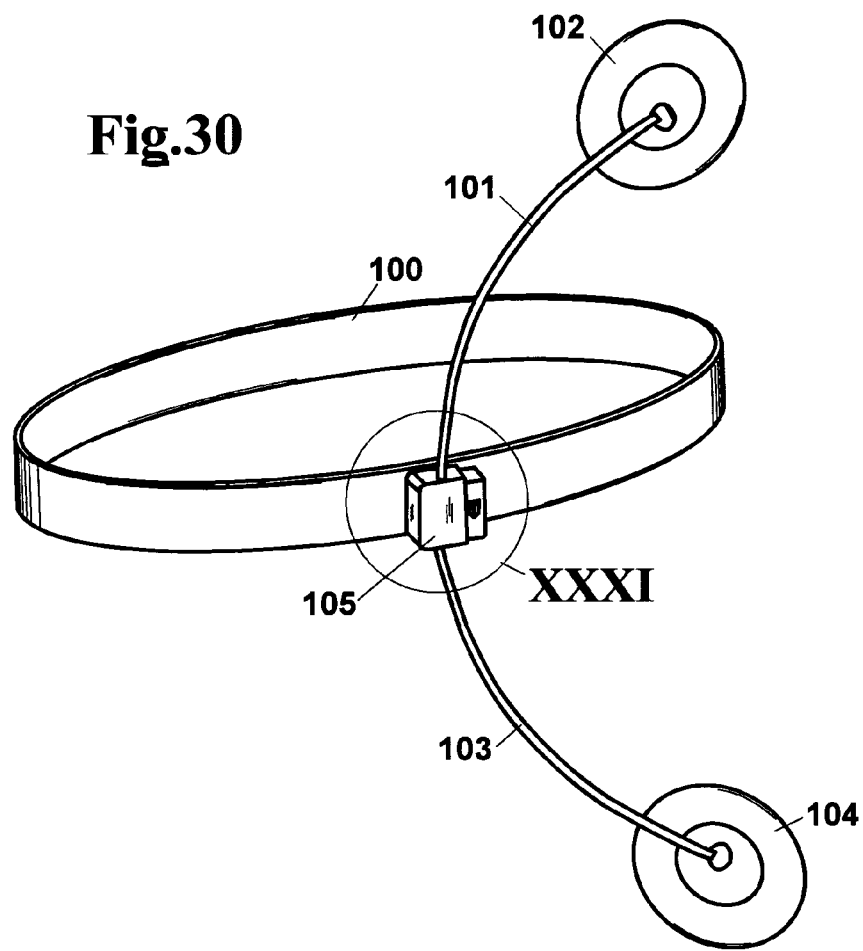
FIG. 30 shows a support belt for a base body and the relative electrode sensors.

Similarly, as shown in FIG. 30, belt 100 comprises sensors for detecting physiological parameters and, as in case of bracelet 80, a connecting portion 105 with base body 1, as shown in detail in FIG. 31, which is adapted to electrically connect the sensors to the base body. In particular, the sensors are a couple of detection electrodes 102 and 104, that are wired to connection portion 105 by means of respective wires 101 and 103, for measuring the impedance of the patient's body in a patient 21, as it is visible in FIG. 32.

In a possible embodiment, belt 100 and bracelet 80 can be adjustable in length and a mutual coupling with a housing (not shown) can be provided on the respective connection portion 80 and 105, which in addition to fasten the belt/bracelet to the patient also operates the sensor, if present.

In a further exemplary embodiment bracelet 80 and belt 100 can be made up of two parts that are mutually connected by means of quickly releasable fastening means. This way, they can be adjusted in order to easily and quickly adapt to the wrist 90 or torso of patient 21, without hampering or blocking the patient's movements.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A physiological monitoring device comprising:
   a first base configured to be removably coupleable to a patient, the first base including
   a first face having a first port,
   a second face having a second port,
   a third face having a third port, the first port and the second port having an identical configuration,
   a controller configured to communicate with a wireless network, and
   a storage unit configured to communicate with the controller; and
   a first physiological monitoring module removably coupleable to the first port or the second port, the first physiological monitoring module including
   an ECG sensor configured to acquire ECG signals from the patient,
   a first interface compatible with the first port and the second port, and
   a first identification device on the interface,
   the first physiological monitoring module configured to communicate with the controller to wirelessly communicate the ECG signals acquired from the patient to the wireless network,
   the controller configured to identify whether the first physiological monitoring module is in the first port or the second port based on the first identification device,
   the controller further configured to wirelessly communicate with the wireless network that the first physiological monitoring module is connected to the first base and the type of data to be transmitted;
   wherein the first identification device comprises at least a pin coupleable to a corresponding pin on either the first face or the second face to exchange electrical communication, wherein the pin on either the first face or the second face receives a signal from the first physiological module, the signal identifying the first physiological module.

2. The physiological monitoring device of claim 1, further comprising a second physiological monitoring module separately removably coupleable to the first port or the second port, the second physiological monitoring module including a second sensor configured to acquire non-ECG physiological signals from the patient, a second interface compatible with the first port and the second port, and a second identification device on the second interface, the second physiological monitoring module configured to communicate with the controller to wirelessly communicate the non-ECG physiological signals acquired from the patient to the wireless network, the controller configured to identify whether the second physiological monitoring module is in the first port or the second port based on the second identification device, the controller further configured to wirelessly communicate with the wireless network that the second physiological monitoring module is connected to the first base and the type of data to be transmitted, wherein the second identification device comprises at least a pin coupleable to a corresponding pin on either the first face or the second face to exchange electrical communication, wherein the pin on either the first face or the second face receives a signal from the second physiological module, the signal identifying the second physiological module.

3. The physiological monitoring device of claim 1, wherein the first physiological monitoring module is removably coupleable to the third port.

4. The physiological monitoring device of claim 2, wherein the second sensor is configured to measure at least one of temperature, movement, position, and blood pressure.

5. The physiological monitoring device of claim 2 wherein the first interface includes a first connector, and wherein the second interface includes a second connector, and wherein the first connector and the second connector are identical and are receivable in the first port and the second port.

6. The physiological monitoring device of claim 2, wherein:
the first face of the base defines a first recess;
the first physiological monitoring module includes a first tooth,
the second face of the base defines a second recess,
the second physiological monitoring module includes a second tooth,
wherein the first tooth and the second tooth are configured to be received by the first recess and the second recess.

7. The physiological monitoring device of claim 1, further comprising an adapter separately removably coupleable to the first port or the second port, the adapter configured to removably receive a second physiological monitoring module, the second physiological monitoring module configured to communicate with the controller to wirelessly communicate physiological data acquired from the patient to the wireless network.

8. The physiological monitoring device of claim 1, further comprising:
a second base;
a bridge module removably coupled between the first base and the second base; and
a second physiological monitoring module removably coupleable to the second base, the controller of the first base configured to receive physiological data acquired from the patient by the second physiological monitoring module,
wherein the bridge module is configured to transmit communication between the second base and the first base.

9. A physiological monitoring device comprising:
a base configured to be removably coupleable to a patient, the base including
a plurality of ports having an identical configuration,
a controller configured to communicate with a wireless network, and
a storage unit configured to communicate with the controller;
a first physiological monitoring module separately removably coupleable to any one of the ports, the first physiological monitoring module including a sensor configured to acquire first signals associated with a first physiological parameter of the patient, a first interface compatible with the ports, and a first identification device on the first interface, the first physiological monitoring module configured to communicate with the controller to wirelessly communicate the first signals associated with the first physiological parameter acquired from the patient to the wireless network, the controller configured to identify which port the first physiological monitoring module is connected to based on the first identification device, the controller further configured to wirelessly communicate with the wireless network that the first physiological monitoring module is connected to the base and the type of data to be transmitted; and
a second physiological monitoring module separately removably coupleable to any one of the ports, the second physiological monitoring module including a sensor configured to acquire second signals associated with a second physiological parameter of the patient that is different from the first physiological parameter, a second interface compatible with the ports, and a second identification device on the second interface, the second physiological monitoring module configured to communicate with the controller to wirelessly communicate the second signals associated with the second physiological parameter acquired from the patient to the wireless network, the controller configured to identify which port the second physiological monitoring module is connected to based on the second identification device, the controller further configured to wirelessly communicate with the wireless network that the second physiological monitoring module is connected to the base and the type of data to be transmitted;
wherein each of the first and second identification devices comprises at least a pin coupleable to a corresponding pin on any of the ports to exchange electrical communication, wherein the pin on any of the ports receives a signal from the first or second physiological module, the signal identifying one of the first or second physiological modules, respectively.

10. The physiological monitoring device of claim 9, wherein the base includes a plurality of faces, and wherein the plurality of ports are arranged on different faces of the base.

11. The physiological monitoring device of claim 9, wherein each of the plurality of ports is configured to automatically identify and communicate bidirectionally with each of the first physiological monitoring module and the second physiological monitoring module when each of the first physiological monitoring module and the second physiological monitoring module are coupled to the base.

12. The physiological monitoring device of claim 9, wherein the first physiological parameter is selected from the group consisting of temperature, ECG, movement, position, and blood pressure.

13. The physiological monitoring device of claim 12, wherein the second physiological parameter is selected from the group consisting of temperature, ECG, movement, position, and blood pressure.

14. The physiological monitoring device of claim 9 wherein the first interface includes a first connector and wherein the second interface includes a second connector, and wherein the first connector and the second connector are identical and are separately receivable in any one of the plurality of ports on the base.

15. A physiological monitoring device comprising:
a first base configured to be removably coupleable to a patient, the first base including
a first face having a first port,
a second face having a second port,
a third face having a third port, the first port and the second port having an identical configuration,
a controller configured to communicate with a wireless network, and
a storage unit configured to communicate with the controller;
a first physiological monitoring module removably coupleable to the first port or the second port, the first physiological monitoring module including a first sensor configured to monitor a first physiological parameter of the patient, a first interface compatible with the first port and the second port, and a first identification device on the interface, the first physiological monitoring module configured to communicate with the controller to wirelessly communicate physiological data related to the first physiological parameter acquired from the patient to the wireless network, the controller configured to identify whether the first physiological monitoring module is in the first port or the second port based on the first identification device, the controller further configured to wirelessly communicate with the wireless network that the first physiological monitoring module is connected to the first base and the type of data to be transmitted;
wherein the first identification device comprises at least a pin coupleable to a corresponding pin on either the first face or the second face to exchange electrical communication, wherein the pin on either the first face or the second face receives a signal from the first physiological module, the signal identifying the first physiological module;
a second base;
a bridge module removably coupleable between the first base and the second base;
a second physiological monitoring module removably coupleable to the second base, the second physiological monitoring module including a second sensor configured to monitor a second physiological parameter of the patient that is different from the first physiological parameter, the second base configured to transmit data related to the second physiological parameter to the first base via the bridge module.

16. The physiological monitoring device of claim 15, wherein the bridge module is configured to transmit communication between the second base and the first base.

17. The physiological monitoring device of claim 15, wherein when the first physiological monitoring module couples to the first base, the first base is configured to automatically identify and communicate bidirectionally with the first physiological monitoring module.

18. The physiological monitoring device of claim 15, wherein the first sensor is configured for detecting one of temperature, ECG, movement, position, and blood pressure, and wherein the second sensor is configured for detecting one of temperature, ECG, movement, position, and blood pressure.

19. The physiological monitoring device of claim 9, wherein the first physiological monitoring module is coupleable to a first port of the plurality of ports at the same time that the second physiological monitoring module is coupleable to a second port of the plurality of ports.

20. The physiological monitoring device of claim 19, wherein the first physiological monitoring module has a higher processing priority than the second physiological monitoring module.

* * * * *